US009924723B2

(12) United States Patent
Hernandez et al.

(10) Patent No.: US 9,924,723 B2
(45) Date of Patent: Mar. 27, 2018

(54) DELIVERY OF HEAVY METALS FOR THE INHIBITION OF MICROBIALLY INDUCED CONCRETE CORROSION

(71) Applicant: THE REGENTS OF THE UNIVERSITY OF COLORADO, A BODY CORPORATE, Denver, CO (US)

(72) Inventors: Mark Hernandez, Boulder, CO (US); Alison Ling, Minneapolis, MN (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 15/036,026

(22) PCT Filed: Nov. 11, 2014

(86) PCT No.: PCT/US2014/064928
§ 371 (c)(1),
(2) Date: May 11, 2016

(87) PCT Pub. No.: WO2015/070196
PCT Pub. Date: May 14, 2015

(65) Prior Publication Data
US 2016/0286818 A1 Oct. 6, 2016

Related U.S. Application Data

(60) Provisional application No. 61/902,673, filed on Nov. 11, 2013.

(51) Int. Cl.
*A01N 59/16* (2006.01)
*B05D 7/00* (2006.01)
(Continued)

(52) U.S. Cl.
CPC .............. *A01N 59/16* (2013.01); *B05D 7/00* (2013.01); *C04B 28/04* (2013.01); *C04B 41/009* (2013.01);
(Continued)

(58) Field of Classification Search
None
See application file for complete search history.

(56) References Cited

U.S. PATENT DOCUMENTS 5,797,238 A     8/1998  Berntsson et al.
2002/0069791 A1* 6/2002  Merkley ................. C04B 18/24
                                                        106/657
(Continued)

FOREIGN PATENT DOCUMENTS

CN      101371956 A   *   2/2009
JP      08184165 A    *   7/1996
(Continued)

OTHER PUBLICATIONS

Hawley's Condensed Chemical Dictionary, 2007, no author.*
(Continued)

*Primary Examiner* — David Sample
(74) *Attorney, Agent, or Firm* — Saul Ewing Arnstein & Lehr LLP; Kathryn Doyle; Domingos J. Silva

(57) ABSTRACT

The present invention provides concrete-containing compositions, and methods of making and using the same, that allow for the prevention of microbially induced corrosion in concrete. In certain embodiments, the concrete-containing compositions comprise a cementitious substrate, and a formulation of heavy metal-laden, carbon-based sorbent.

20 Claims, 11 Drawing Sheets

(51) Int. Cl.
    *C04B 41/50* (2006.01)
    *C04B 28/04* (2006.01)
    *C04B 41/00* (2006.01)
    *C04B 41/48* (2006.01)
    *C04B 41/63* (2006.01)
    *C04B 41/65* (2006.01)
    *C04B 111/20* (2006.01)
    *C04B 111/74* (2006.01)

(52) U.S. Cl.
    CPC ...... *C04B 41/4853* (2013.01); *C04B 41/5001* (2013.01); *C04B 41/5007* (2013.01); *C04B 41/5076* (2013.01); *C04B 41/5098* (2013.01); *C04B 41/63* (2013.01); *C04B 41/65* (2013.01); C04B 2111/2092 (2013.01); C04B 2111/74 (2013.01)

(56) References Cited

U.S. PATENT DOCUMENTS

2004/0103823 A1   6/2004  Kurihara et al.
2006/0048671 A1   3/2006  Ong
2006/0188580 A1*  8/2006  Sacks .................. A01N 25/12
                                                    424/489
2007/0027224 A1   2/2007  Cowan et al.
2009/0294743 A1*  12/2009  Galvan Cazares ..... C04B 28/04
                                                    252/520.3

FOREIGN PATENT DOCUMENTS

KR    1020100115644 A  *  10/2010
WO      2014063114 A1     4/2014

OTHER PUBLICATIONS

Cellulose Granular Absorbent, http://www.oildri.net/Gran_Cellulose.html, 2009 no author.*
Haile, et al., "Evaluation of the Bactericidal Characteristics of Nano-Copper Oxide or Functionalized Zeolite Coating for Bio-Corrosion Control in Concrete Sewer Pipes", Corrosion Science, vol. 52, 2010, pp. 45-53.
Haile, et al., "The Inhibitory Effect of Antimicrobial Zeolite on the Biofilm of Acidithiobacillus thiooxidans", Biodegradation, vol. 21, 2010, pp. 123-134.

* cited by examiner formulation applied as a concrete admixture formulation applied in cementitious surface coating formulation applied in non-cementitious surface coating (i.e. epoxy)

DELIVERY OF HEAVY METALS FOR THE INHIBITION OF MICROBIALLY INDUCED CONCRETE CORROSION

CROSS-REFERENCE TO RELATED APPLICATIONS

This Application is a 35 U.S.C. § 371 national phase application from, and claims priority to, International Application No. PCT/US2014/064928, filed Nov. 11, 2014, and published under PCT Article 21(2) in English, which claims priority under 35 U.S.C. § 119(e) to U.S. Provisional Application No. 61/902,673, filed Nov. 11, 2013, all of which applications are is incorporated by reference herein in their entireties.

I. BACKGROUND

The maintenance and replacement of damaged concrete sewer pipes and related structures carries significant infrastructure liabilities for metropolitan areas all over the globe. In a 1989 survey of 89 wastewater utilities in the United States, 63% reported active corrosion prevention programs to rehabilitate concrete pipe corrosion, and 70% reported corrosion at various sites within their treatment plants. Since this time, reports of corrosion have continued to increase. Wastewater collection systems in the United States consist of about 800,000 miles of sewers and 12 million wastewater manholes. About 25% of this infrastructure is over 40 years old, and over 80% is concrete. Sewer pipes typically run below streets or developed property, so repair and replacement procedures can disrupt community economic activity. In addition, hydrogen sulfide released from wastewater collection systems can threaten environmental health as well as cause aesthetic problems.

Concrete corrosion often occurs as a result of microbially mediated sulfur cycling within wastewater collection systems. Sulfate present in wastewater is oxidized to sulfide in anoxic biofilms below the waterline. This sulfide can partition into the pipe headspace as $H_2S$ (hydrogen sulfide) gas, which serves as a substrate for acidogenic sulfur oxidizing bacteria above the waterline. These bacteria produce sulfuric acid which chemically alters the cement binder and weakens the concrete pipe. This is biogenic sulfuric acid when produced by microbes; it is as potent as any manufactured acid, and reacts with calcium and aluminum oxides in the cured cement to produce corrosion products of gypsum, ettringite, and monosulfoaluminate, which increase the concrete volume, decrease its density and undermine structural stability. Corrosion products can be washed away at higher flows, resulting in decreased mass and reduced pipe thickness.

Depending on the degree of structural deterioration, a corroded pipe must either be repaired, rehabilitated, or replaced; otherwise extreme corrosion progresses into structural failure scenarios. Concrete additives and coatings have been developed in the prior art in an attempt to impair the growth of biofilms in new concrete structures and to rehabilitate damaged structures. These prior art methods fall into three general categories: a) use of corrosion-resistant pipe materials, b) surface coatings and linings, and c) antimicrobial concrete additives.

As an alternative to concrete pipe, polymer-based pipe materials such as polyvinyl chloride (PVC), fiberglass, and high-density polyethylene (HDPE) are not susceptible to acid attack and are thus resistant to corrosion. However, the cost of these materials is significantly higher than the cost of reinforced concrete pipe, and their structural strength is inferior.

Prior to the present disclosure protective surface coatings were applied to concrete such as, for example, the inner concrete surface of concrete pipe, to prevent corrosion by placing a physical barrier between biogenic sulfuric acid and the concrete surface. Application methods include spraying, painting, and slip-lining. Adequate surface preparation and effective application are important with this rehabilitation approach, as any leaks in the coating allows corrosion to continue beneath the coating. Accomplishing such uniform coating is especially difficult in the sewer environment as a result of variable temperature, moisture, and the need to divert flow while work is conducted. Surfaces can be prepared for coating by high-pressure washing, which removes corrosion product, biofilm growth, grease and dirt. Materials used for pipe surface coatings include epoxy, polyurethane, polyurea, and coal tar. Protective coatings are intended to be resistant to acid attack, and experience less corrosion under simulated biological and abiotic corrosive conditions than uncoated concrete. Epoxy is cured with heat or through polymerization with amines or polyamides. It is durable and resistant to acid, abrasion, and moisture; resistance is correlated with high solids content. Spray-on linings of either cementitious (i.e., shotcrete) or polymeric nature are another common rehabilitation method, as they are easier to apply and cure. A popular rehabilitation method is slip-lining degraded pipe with a cure-in-place pipe (CIPP) plastic liner, which is both structurally supportive and resistant to corrosion. This method is documented under ASTM Standard F-1216. After the corrosion products are removed, a lining is placed in the sewer pipe and cured by UV light. CIPP lining materials include reinforced polyethylene, polyvinyl chloride, and carbon/fiberglass.

Antimicrobial treatments for concrete include the use of metals or other "antimicrobials" to inhibit the growth of sulfide-oxidizing microbes responsible for biogenic sulfuric acid production. For example, antibiotic-loaded fibers (MicrobanB) inhibit bacterial growth using triclosan—an antibiotic that is also used in personal care products. As another example, zeolites are aluminosilicate adsorbent materials that are used in the corrosion industry to (slowly) deliver toxic heavy metal ions such as copper and silver to the concrete surface over a pipe's service life. Concrete mortars treated with either technology and inoculated with sulfide-oxidizing cultures exhibit reduced levels of adenosine triphosphate (ATP)—an indicator of microbial activity—when compared to untreated cement mortar. Silver zeolites also inhibit the growth of *Acidithiobacillus thiooxidans* and other bacterial cultures. Heavy metal oxides (copper and silver) mixed with commercial epoxy have been shown to inhibit sulfate-reducing cultures, but have not been tested with sulfide-oxidizing cultures. These methods fare well in laboratory and small-scale tests, but are typically more expensive than epoxy or polyurea lining Another product called ConMicShield uses silicone quaternary ammonium salts to kill bacteria electrostatically and has been widely applied to inhibit corrosion-causing bacteria. ConMicShield can be added to concrete mix prior to curing or applied retroactively using shotcrete.

The foregoing examples of the related art and limitations related therewith are intended to be illustrative and not exclusive. Other limitations of the related art will become apparent to those of skill in the art upon a reading of the specification and a study of the drawings.

II. SUMMARY

The present application is generally related to inhibiting the acidogenic microbes that cause concrete corrosion (dissolution of cement) and, more particularly, to advanced methods, structures and materials employing carbon-based sorbents that, when loaded with heavy metals to protect concrete from microbially induced corrosion (MICC).

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 3A:
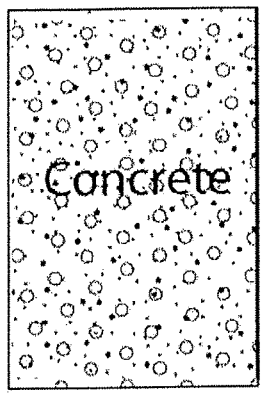
Figure 3B:
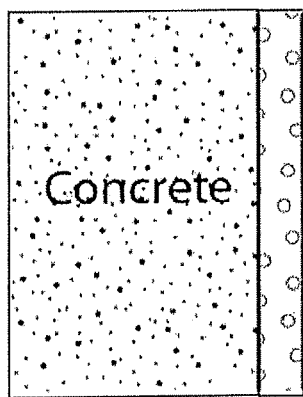
Figure 3C:
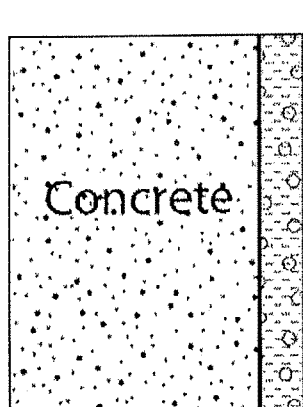

FIGS. 3a-3c are diagrammatic views, in elevation, that illustrate various embodiments of protected structures in accordance with the present disclosure. Throughout these figures, the metal-sorbent formulation, according to the present disclosure, is illustrated by circles with a white fill. FIG. 3a illustrates a protected structure 200 wherein a formulation is added to concrete as an admixture such that the structure is integrally protected. FIG. 3b illustrates a protected structure 204 wherein a cementitious surficial coating containing the formulation 208 is applied to a concrete substrate 212. FIG. 3c is an illustration of a protected structure 216 wherein a non-cementitious surficial coating containing the formulation 220 is applied to concrete substrate 212.

Figure 4:
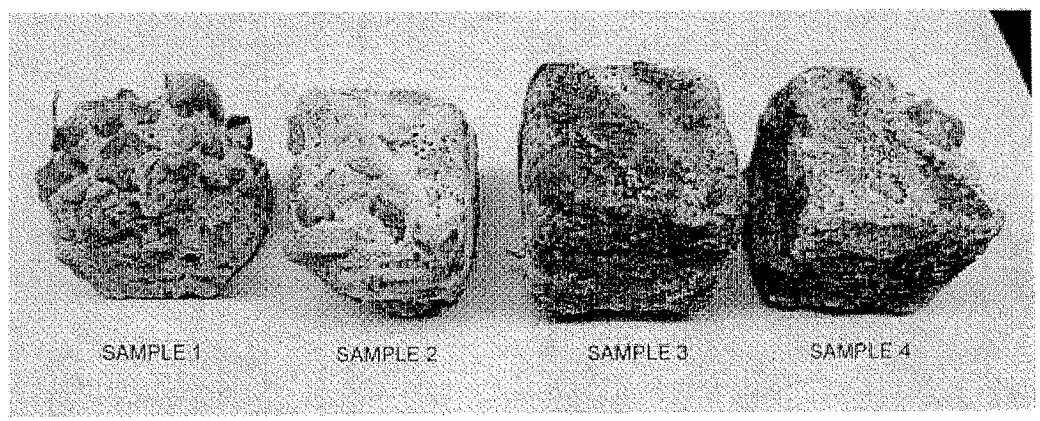

FIG. 4 is a photograph illustrating four samples wherein each sample was exposed to the same corrosive environment for the same amount of time. Sample 1 was an untreated concrete sample; Sample 2 was treated with GAC (no metals); Sample 3 was treated with cadmium-laden GAC; Sample 4 was treated with chromium-laden GAC.

Figure 5:
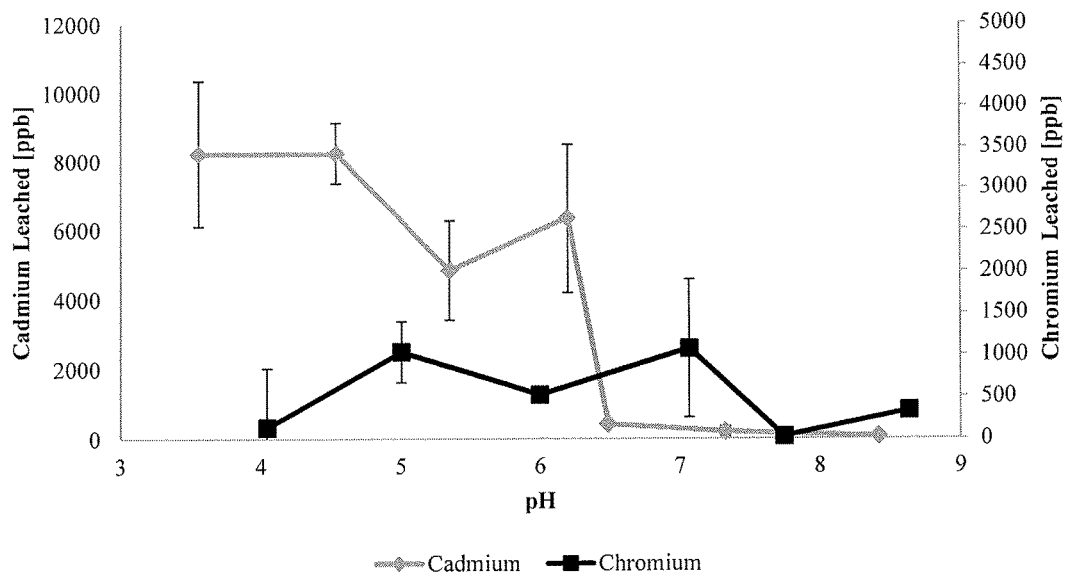

FIG. 5 shows metal leached from GAC pre-loaded with cadmium (✱) or chromate (■) ions in buffered solutions at various pH values. Phosphate or citrate buffering was used to stabilize pH. Points represent the mean of three observations. Error bars indicate standard deviation.

Figure 6:
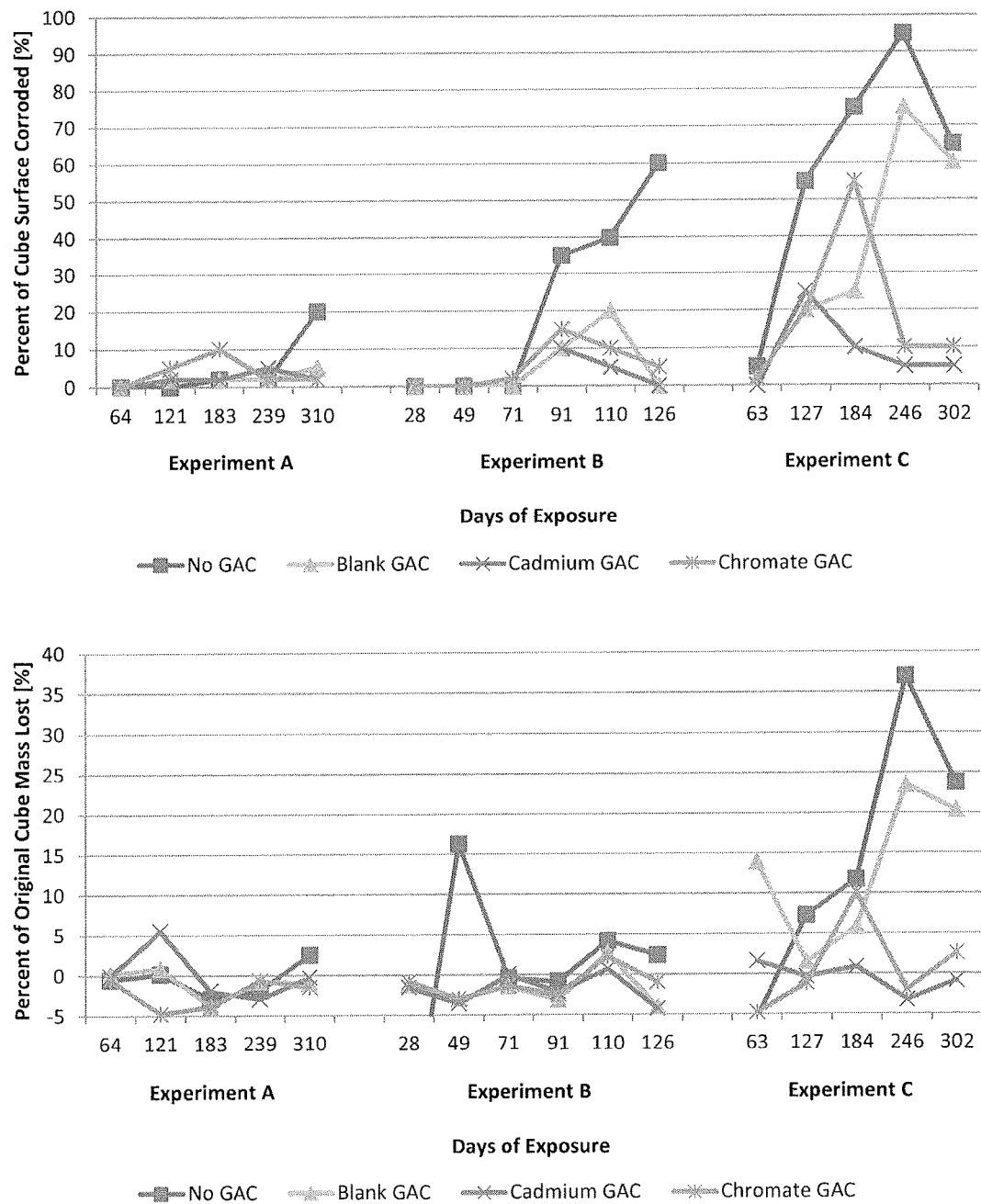

FIG. 6 shows a comparison of percent of surface corroded and percent of original mass lost for untreated concrete specimens (red and green) and for specimens treated with a surficial application of a metal-carbon formulation (purple and blue). (■) No GAC control; (Δ) GAC without metal; (x) GAC impregnated with cadmium cations; (*) GAC impregnated with chromate anions.

Figure 7:
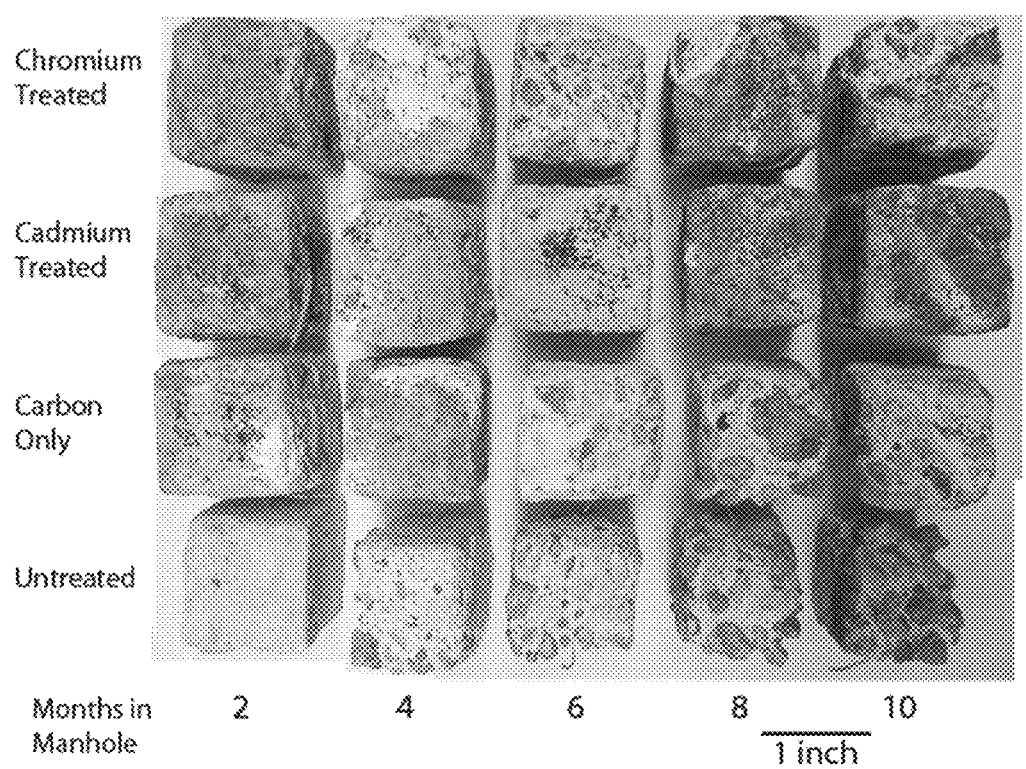

FIG. 7 shows concrete cubes following exposure in the MH1 (Experiment 3, $H_2S$ concentrations>300 ppm) for two to ten months. Specimens were removed from the manhole and taken to the lab for analysis. Photograph shows specimens after corrosion product was removed and specimens were dried.

Figure 8:
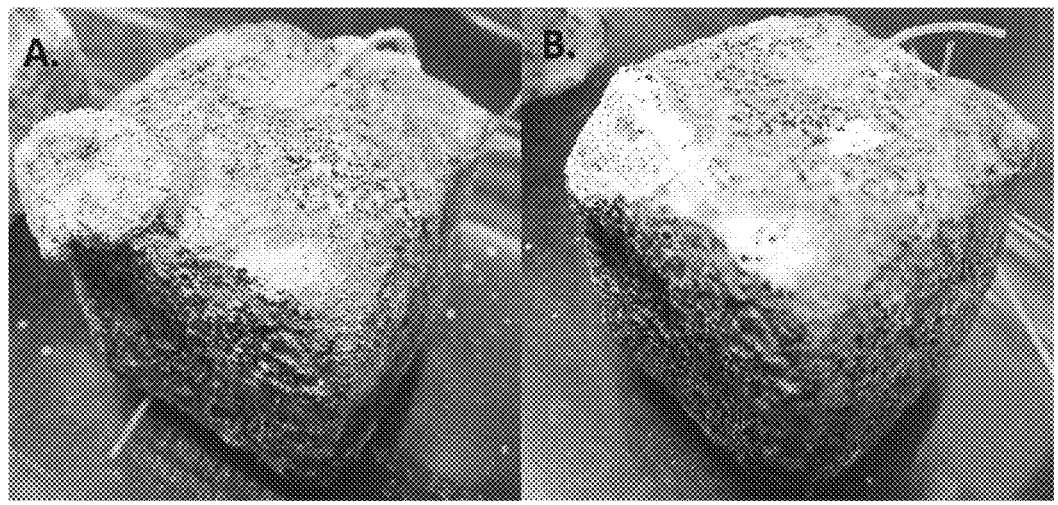

FIG. 8 shows example specimens treated with metal-GAC formulation that experienced corrosion only where surface directly contacted PVC casing (upper-left of cube). This cadmium-GAC treated specimen was exposed for ten months in MH1, and is shown before (A.) and after (B.) removal of corroded layer.

Figure 9:
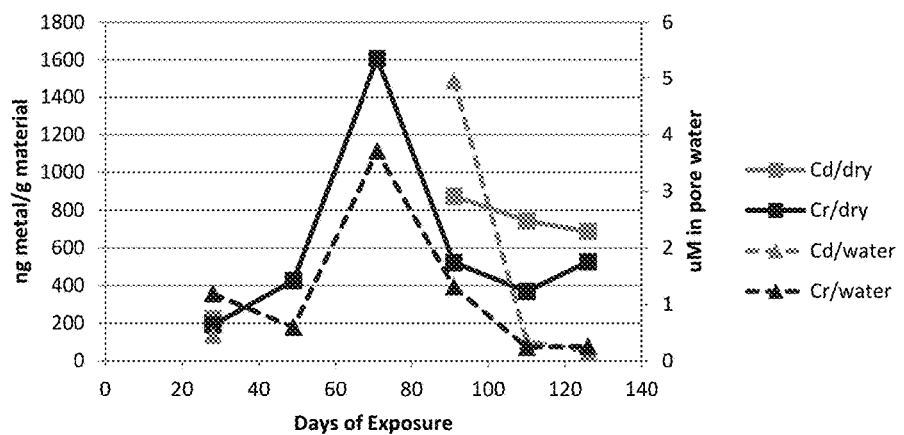

FIG. 9 shows cadmium (grey) and chromium (black) levels at concrete surface in dried, sieved corrosion product as ng metal/g (solid lines) and in pore water as μM (dashed lines) for 26-126 days of exposure in high $H_2S$ atmosphere (Experiment 2) (✻) cadmium in dry fines; (■) chromium in dry fines; (✱) cadmium in pore water; (♦) chromium in pore water. Metal concentrations measured by inductively coupled plasma mass spectrometry (ICP-MS) of acid extracted samples.

Figure 10:
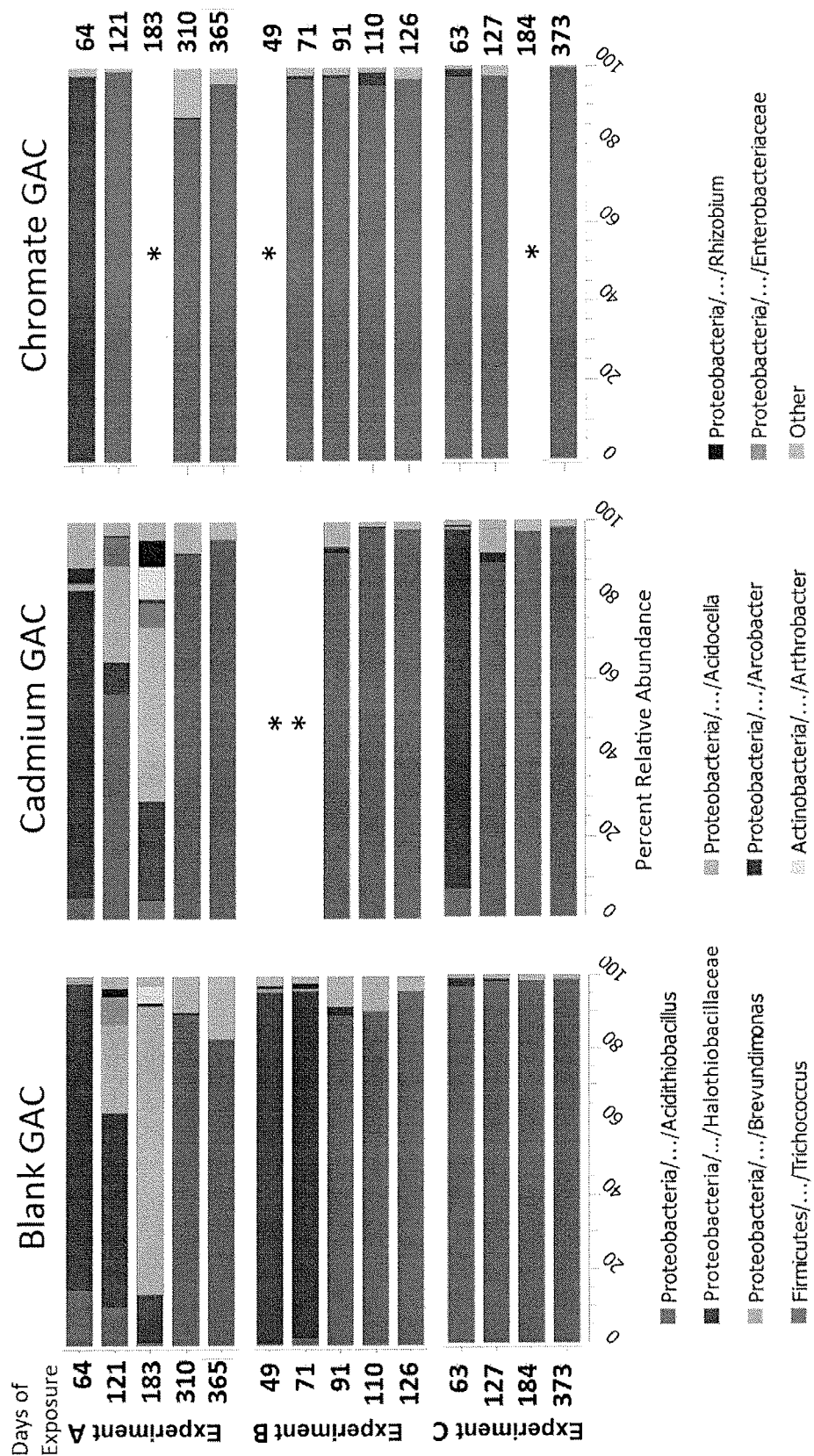

FIG. 10 shows bacterial community succession on otherwise identical specimens incorporating unloaded granular activated carbon (left) and granular activated carbon loaded with cadmium (center) and chromate (right) ions. Taxa definitions based on Illumina MiSeq sequencing of the V1V2 region of bacterial 16S rRNA genes and comparison to SILVA 115NR database. Bar widths indicate percent relative abundance of microbial taxa in sample libraries; bar colors indicate taxa identity. * indicates missing data due to low DNA recovery.

Figure 11:
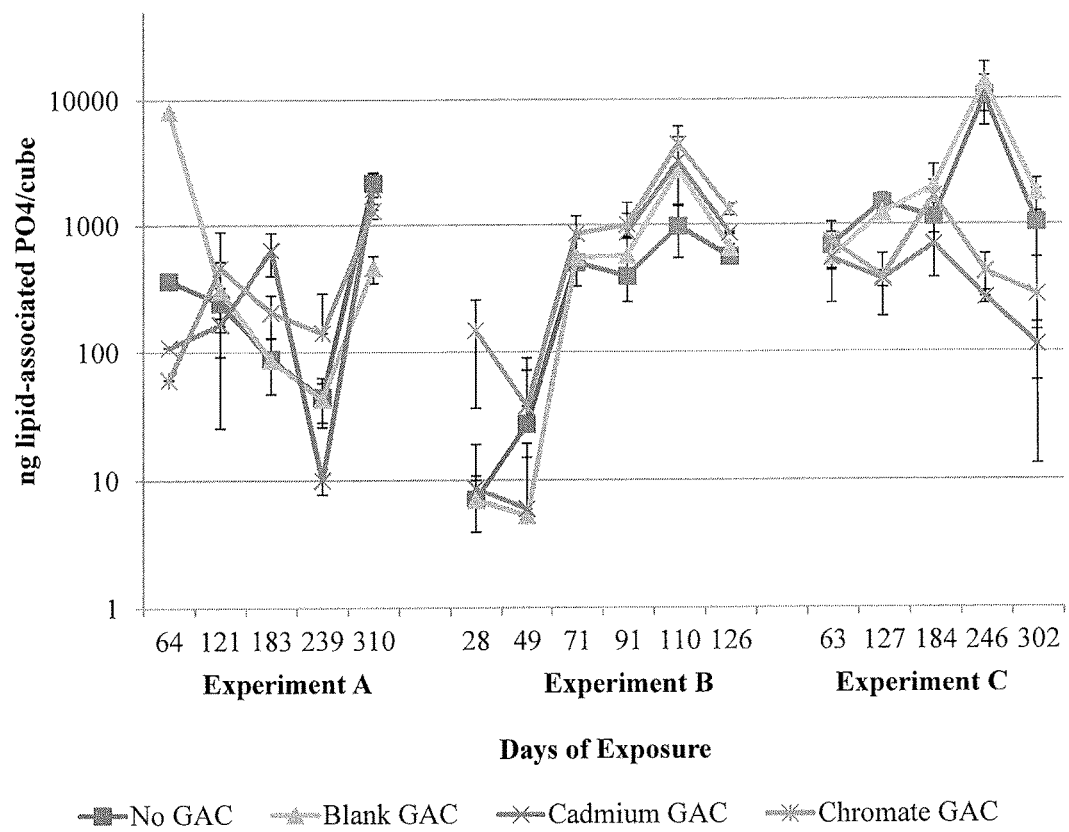

FIG. 11 shows lipid-associated phosphate per cube (indicator for biomass) for control concrete specimens (red and green) and concrete specimens treated with metal-carbon formulation (purple and blue) exposed for up to ten months in high H2S sanitary manholes. (■) No GAC control; (Δ) GAC without metal; (x) GAC impregnated with cadmium cations; (*) GAC impregnated with chromate anions.

Figure 12:
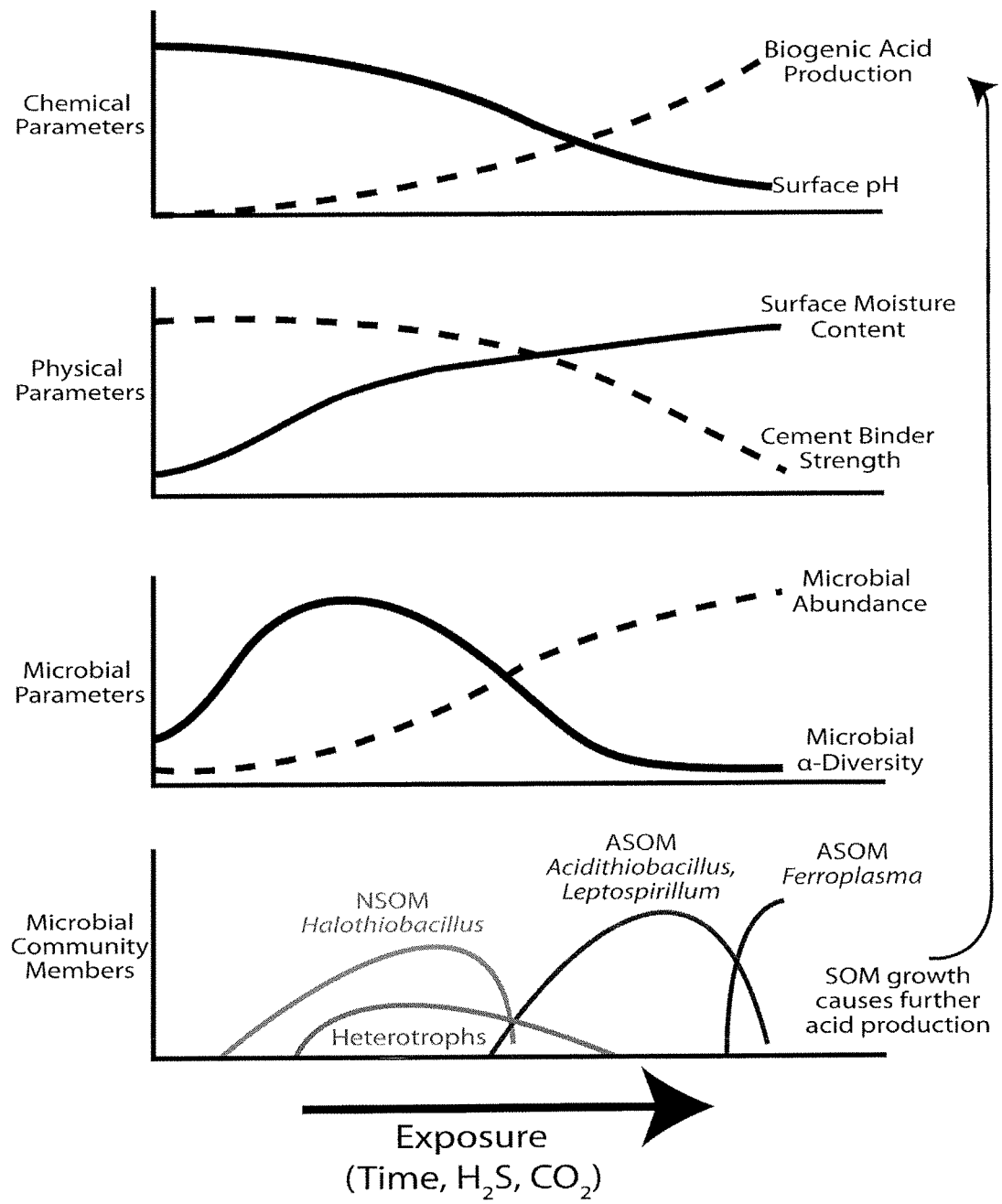

FIG. 12 shows the juxtaposition of chemical, physical, and microbial changes associated with increased exposure (composite of time, H2S, and CO2) in microbially induced concrete corrosion

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10"

is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The following description is presented to enable one of ordinary skill in the art to make and use the invention and is provided in the context of a patent application and its requirements. Various modifications to the described embodiments will be readily apparent to those skilled in the art and the generic principles taught herein may be applied to other embodiments. Thus, the present invention is not intended to be limited to the embodiments shown, but is to be accorded the widest scope consistent with the principles and features described herein including modifications and equivalents. It is noted that the drawings are not to scale and are diagrammatic in nature in a way that is thought to best illustrate features of interest. Descriptive terminology may be used with respect to these descriptions, however, this terminology has be adopted with the intent of facilitating the reader's understanding and is not intended as being limiting.

The present application brings to light the heretofore unseen utilization of carbon-based sorbent material pre-loaded with heavy metal ions to deliver toxicity to concrete corroding microbes in a pH-dependent manner, and thus impair microbially induced corrosion of cementitious materials. Such corrosion may be referred to herein as microbially induced corrosion of concrete (MICC). Thus, in one aspect, disclosed herein are protected structures for use in an environment that subjects protected structure to microbially induced concrete corrosion. In its most simplistic form, the protected structure can comprise a substrate and a sorbent.

In one embodiment, the substrate can comprise a cementitious material. Examples, of cementitious materials include non-hydraulic cements such as, for example, slaked lime and hydraulic cements, including but not limited to concrete, shotcrete, stucco, mortars, Portland cement, Portland cement blends, Portland flyash cement, Portland pozzolan cement, Portand silica fume cement, energetically modified cement, plastic cements, expansive cements (e.g., Portland Clinker), white blended cements, Pozzolan-lime cements, slag-lime cements, High-performance fiber-reinforced cementitious composites, limecrete, vacuum concrete, Calcium sulfoaluminate cements, and Calcium aluminate cements. Thus, in one aspect, disclosed herein are protected structures comprising a concrete substrate.

One embodiment of the subject formulation uses activated carbon as a sorbent material which can be used, for example, to deliver metal ions to corrosive biofilms. Carbon from a variety of sources (including charcoal, nut shells, and fruit stones) can be thermally or chemically activated to yield surface areas over 500 $m^2$ per gram of material. The adsorption of metals onto activated carbon surface sites is dependent on the solution pH, temperature, and carbon characteristics. Generally, cationic metal ions sorb more strongly at high pH, while anion metal ions sorb more strongly at low pH. Other embodiments can use charcoal, bio-char, or other carbon-based sorbents, including but not limited to flyash, which have lower adsorption capacities for heavy metals than activated carbon, but are more affordable and widely available. Thus, any suitable carbon-based sorbent can be used in accordance with the present disclosure.

It is also disclosed herein that the disclosed protected structures can utilize a variety of carbon-based sorbent materials and the use of individual metals or mixtures of metals including, but not limited to cadmium, chromium, zinc, copper, silver, nickel, cobalt, lead, molybdenum, and tungsten. For example, disclosed herein are protected structure comprising cementitious substrate; and a formulation of metal-laden, carbon-based sorbent, wherein the metal-laden, carbon-based sorbent comprises cadmium, chromium, zinc, copper, silver, nickel, cobalt, lead, molybdenum, and tungsten.

As noted above, in one aspect, for example, disclosed herein are heavy metal-laden, carbon metal-laden, carbon-based sorbent materials comprising powdered activated carbon (PAC) or granular activated carbon (GAC) loaded with cadmium ($Cd^{2+}$) or chromate ($CrO_4^{2-}$) ions. Thus, in one aspect, disclosed herein are protected structures comprising a heavy metal-laden, carbon-based sorbent. For example, disclosed herein are protected structure comprising cementitious substrate and a formulation of heavy metal-laden, carbon-based sorbent, wherein the heavy metal-laden, carbon-based sorbent comprises cadmium (such as, for example, cadmium sulfate ($CdSO_4$)) or chromate (such as for example, potassium chromate ($K_2CrO_4$)).

Formulations of the present disclosure can be produced by mixing a sorbent material with a metals solution at neutral pH (7-9) for at time period, by way of example, from 8-48 hours. The metal or metals can be obtained, for example, from industrial waste or metal salts. If industrial metals pickling liquors or plating waste are used, this waste can be basified in order to provide the neutral pH. The sorbent can then be removed from the metals solution, rinsed with water several times, and dried, by way of non-limiting example, at 60° C. for at least 24 hours. At this point, the metals-sorbent formulation is ready for addition to concrete for casting new structures, forming precast components and/or for addition to cementitious or non-cementitious coatings for surface treatment of new or old structures.

It is understood and herein contemplated that the amount of metal used in the metal-laden carbon sorbent material can vary depending on the intended application environment. As the pH of the application environment drops, it is appreciated that the amount of metal leaching increases and the inhibitory concentration also decreases. Accordingly, the amount of a given metal needed in a metal-laden carbon sorbent material to be used at a pH of 3 is less than the amount of that same metal needed in a metal-laden carbon sorbent material at a pH of 5 (see, for example, Table 1). In one aspect, the inhibitory concentration of metal leached into the system can be, for example, from about 0.3 to 10.0 ug/cm3 of copper, from about 0.1 to 6.0 ug/cm3 of cadmium, from about 4.0 to 20.0 ug/cm3 of zinc, and from about 0.1 to 5.0 ug/cm3 of nickel, where the medium is solid, semi-solid, a conglomerate or hydrogel (for instance biofilm, cement, concrete, corrosion products thereof, or any associated combination), including or not-including condensates from the environment. For example, the metal concentration can be at least 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.5, 4.0, 4.5, 5.0, 6.0, 7.0, 8.0, 9.0, or 10.0 ug/cm3 or any amount in between of copper; at least 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.5, 4.0, 4.5, 5.0, 5.5, or 6.0 ug/cm3 or any amount in between of cadmium; at least 4.0, 4.1, 4.2, 4.3, 4.4, 4.5, 5.0, 5.5, 6.0, 6.5, 7.0, 7.5, 8.0, 8.5, 9.0, 9.5, 10, 11, 12, 13, 14, 15, 16, 17, 18, 19, or 20 ug/cm3 or any amount in between of zinc; at least 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.5, 4.0, 4.5, or 5.0 ug/cm3 or any amount in between of nickel. It is appreciated herein that the skilled artisan understands how to adjust the amount of metal in the formulation to result in a given concentration for a particular application and can adjust the amount of metal in the carbon-based sorbent material accordingly.

It should be appreciated that embodiments of the disclosed manufacturing process enable beneficial reuse of metals from industrial plating waste streams that are otherwise disposed of as hazardous at high cost. These wastes contain large concentrations of heavy metals. These waste streams are generally low pH and must be treated by the responsible company before being discharged to municipal sewers or waterways. Consequently, obtaining these streams for purposes of metals recovery can be low-cost, free, or provided as a valuable service. Activated carbon can be produced inexpensively from a variety of agricultural byproducts. Thus, the formulation can be produced from reused waste products in a low-cost and sustainable manner.

Heavy metal sorption to activated carbon has been well studied in the context of removing metal contaminants from waste streams. The present disclosure intentionally reverses this removal process in a controlled and targeted manner for the express purpose of inhibiting microbially induced corrosion in a way that has been empirically demonstrated to provide remarkable and unexpected results. The present disclosure provides for the concurrent application of microbiological concepts of cellular toxicity, environmental understanding of the concrete corrosion mechanisms, and materials science experience in carbon-metal sorption chemistry, as well as the formulation and practical uses of concrete.

Applicants recognize that various embodiments of the formulation of the present disclosure can use single metals or mixtures of metals to convey toxicity to the acidogenic microbes that cause concrete corrosion, whether they exist in a sessile state (biofilm) or otherwise. Additionally, Applicants have successfully used cadmium and chromium to serve as non-limiting examples in empirical studies, as is described immediately hereinafter.

In an embodiment, the formulation can be incorporated into concrete as an admixture. The concrete can be poured in a suitable form such as, for example, a pipe or wall such that the formulation is present throughout the concrete structure to form an integrally protected or modified concrete structure. In another embodiment, the formulation can be mixed, for example, with cement to form a surficial coating that can be applied to a pre-existing structure to protect the pre-existing structure. In this regard, the formulation can be added to a pre-made surficial coating mixture prior to mixing. In another embodiment, the formulation can be applied in conjunction with a non-cementitious surficial coating or other anti-corrosion treatment, either as an additive to the coating or treatment material, or as a co-surface (not completely covering a surface). With regard to the latter, and by way of example, the formulation can be "sputtered" onto a surface that is to be protected from biogenic acid attack, thereby demonstrating that the application of metal-laden activated carbon is not required to completely cover the material to be protected. That is, the coverage can be a patchwork or patchy. In still another embodiment, a formulation according to the present disclosure can form part of a cement layer serving as a pre-treatment that is applied prior to the application of a non-cementitious surface coating to form a layered protected structure. A pre-existing structure can be coated before being placed into service application or thereafter. For example, the interior of a concrete pipe can receive a surficial coating either before or after entering service. As another example, the pre-existing structure can be the surface of a concrete wall to be subjected to a corrosive environment biogenic or otherwise. The coating can be applied in any suitable manner such as, for example, by spraying, troweling and/or cured-in place liner. Suitable thicknesses can be in the range of 5 to 50 mm, but can be optimized outside this range as tailored for a particular application. The thickness can be based on the amount of metal loading in the formulation, as well as the capacity of the sorbent to release metal in a targeted manner (response to pH, ionic strength or other physical variable such as, for example, temperature). In a surficial coating and/or modified concrete structure, the recommended amount of formulation can be approximately 50 to 200 grams of metal-laden carbon per 1 cubic meter of bulk concrete or 1 to 5 grams per square meter of coating surface, as estimated by field testing of cadmium- and chromium-loaded granular activated carbon applied in a cementitious surficial coating.

As noted above, it is contemplated herein that the heavy metal laden-carbon-based sorbent and the cementitious substrate can be incorporated into a mixture. Thus, in one aspect, disclosed herein are protected structures which can be used, for example, in an environment that subjects the structure to microbially induced concrete corrosion, wherein said structure comprises a cementitious material comprising a mixture of cement and a formulation of heavy metal-laden, carbon-based sorbent. In a further aspect, the cementitious material can be concrete forming an overall protected structure. It is also contemplated herein that the heavy metal-laden, carbon-based sorbent can be applied as a surficial coating to the concrete substrate. Thus, in one aspect, disclosed herein are protected structures which can be used, for example, in an environment that subjects the structure to microbially induced concrete corrosion, wherein said structure comprises a concrete substrate and a surficial coating applied to the concrete substrate, wherein the surficial coating comprises a formulation of a heavy metal-laden, carbon-based sorbent.

Figure 1:
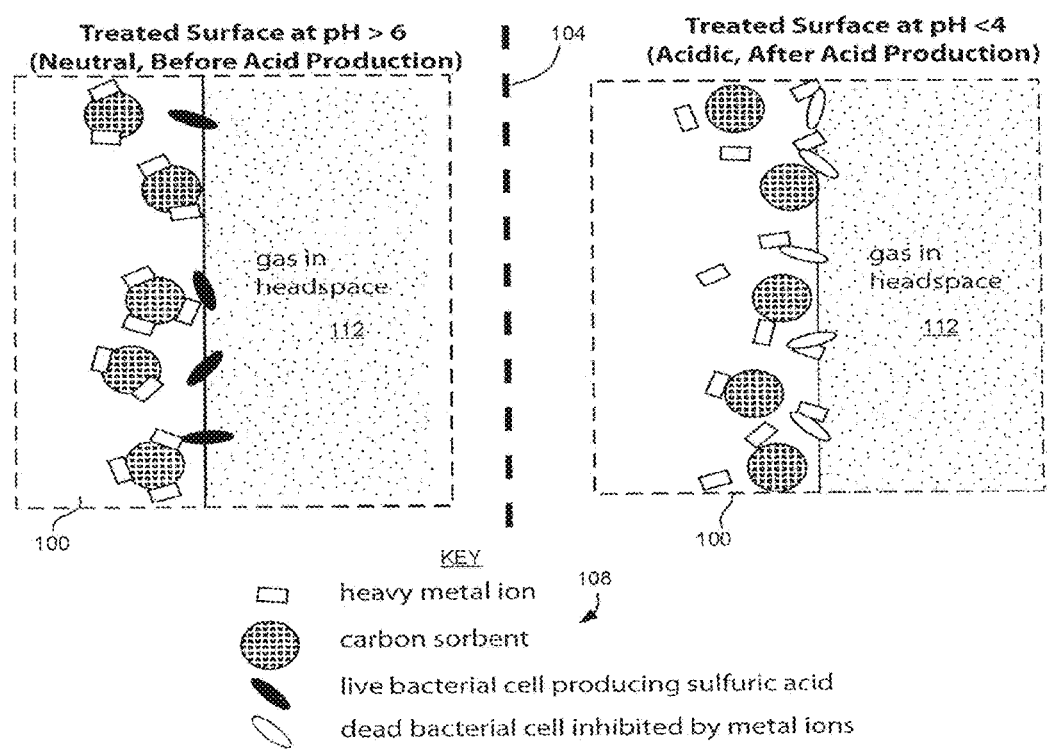
FIG. 1 shows that a protected structure 100, according to the present disclosure is diagrammatically illustrated in a pair of side-by-side elevational views on opposing sides of a dashed line 104.

Referring to FIG. 1, a protected structure 100, according to the present disclosure is diagrammatically illustrated in a pair of side-by-side elevational views on opposing sides of a dashed line 104. It is noted that the protected structure 100 represents any protected structure according to present disclosure including a surficial coating on a concrete substrate or an integrally protected structure having the formulation of the present disclosure distributed throughout the overall structure. A key 108 identifies the various components of the figure. In a first view to the left of line 104, protected structure 100 is exposed to a headspace 112 and has a surface pH that is greater than 6 in an essentially neutral (i.e., near neutral) environment prior to the production of any significant acid by live bacterial and/or fungal cells present, shown as black ovals. In this neutral environment, the heavy metal ions, indicated as rectangles attached to the carbon sorbent are essentially inactive. In a second view to the right of line 104, the surface environment has turned acidic having a pH, for example, less than 4, such that heavy metal ions are liberated from the carbon sorbent and are locally delivered and immediately toxic to the cells, as is illustrated by a heavy metal ion attached to each dead microbial cell.

In one aspect, formulations of metal and sorbent combinations that are suitable in accordance with the present disclosure. In particular, a single metal sorbed to granular activated carbon; a single metal sorbed to a powdered activated carbon; and a single metal sorbed to some other carbon-based sorbent. Also disclosed are mixed metals sorbed to granular activated carbon; mixed metals sorbed to powdered activated carbon; and mixed metals sorbed to some other carbon-based sorbent.

Figure 2:
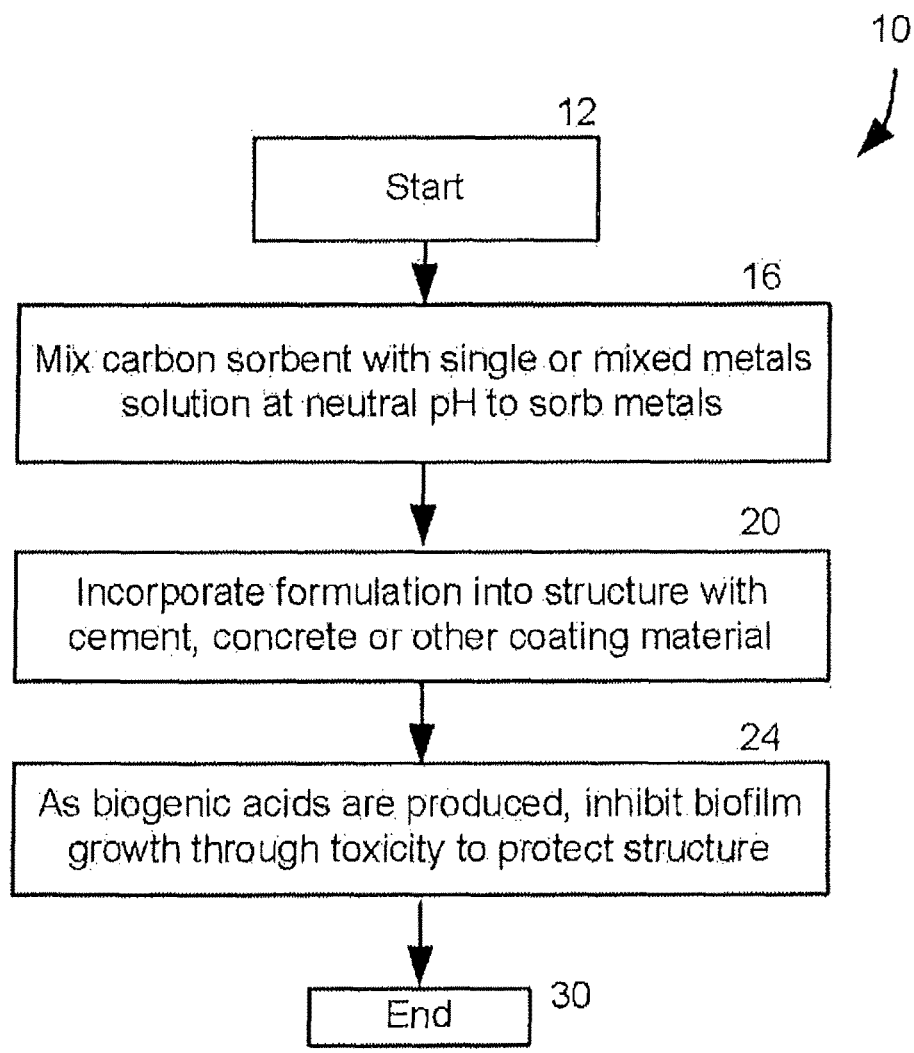
FIG. 2 shows a flow diagram illustrating an embodiment of a method according to the present disclosure.

Turning to the FIG. 2, wherein like components may be indicated by like reference numbers throughout the various views; attention is immediately directed to FIG. 1 which is a flow diagram illustrating an embodiment of a method according to the present disclosure that is generally indicated by the reference number 10. The method begins at 12 and proceeds to 16 at which formulations of the present disclosure can be produced by mixing a carbon-based sorbent material with a metals solution at neutral pH. The latter encompasses a pH range at least approximately from 6 to 9. Following mixing, the formulation of metal-laden sorbent can be removed from the solution and dried in an appropriate manner. At 20, the formulation can be incorporated into a structure which includes any combination of cement, concrete, and surficial treatments for concrete to form a protected structure.

Effective non-cementitious embodiments can use any suitable non-cement supporting mixture to provide a commensurate, pH-apportioned delivery of inhibitory metals to any local environment, which is analogous to cement-based embodiments. Suitable non-concrete supporting mixtures, by way of non-limiting example, include epoxy, polyamine, polyurethane, and coal tar. As shown in FIG. 2, the protected structure is exposed to the potential bioacidogenic environment at 24 such that the formulation that is present in the protected structure serves to generate an environment that is toxic to the microbes which limits their acid production. The method then ends at 30.

Attention is now directed to FIGS. 3a-3c which are diagrammatic views, in elevation, that illustrate various embodiments of protected structures in accordance with the present disclosure. Throughout these figures, the metal-sorbent formulation, according to the present disclosure, is illustrated by circles with a white fill. FIG. 3a illustrates a protected structure 200 wherein a formulation is added to concrete as an admixture such that the structure is integrally protected. FIG. 3b illustrates a protected structure 204 wherein a cementitious surficial coating containing the formulation 208 is applied to a concrete substrate 212. FIG. 3c is an illustration of a protected structure 216 wherein a non-cementitious surficial coating containing the formulation 220 is applied to concrete substrate 212.

In one embodiment, non-cementitious products can be produced, for example, by adding a formulation, according to the present disclosure, to a pre-made non-cementitious coating or other structural formulation. There are a variety of types of such pre-made non-cementitious coatings, but some are epoxy-based liquids that are sprayed onto the concrete surface and cured, using either heat or the prevailing conditions in the structure. The metal-carbon formulation can be added to such a pre-made epoxy mixture prior to application. In another embodiment, the formulation can be applied in a cementitious layer before an the epoxy coating is applied as an overcoat layer to provide protection in the event of epoxy permeation by $H_2S$ gas, which enables acidogenic microbess to grow beneath the epoxy.

Having described embodiments above in detail in accordance with the present disclosure, it is now appropriate to discuss empirical testing performed by Applicants. Cadmium and chromium were utilized for empirical testing purposes in a study, because both are commonly found in a wide variety of industrial waste streams. Cadmium (+II) was chosen for the field test based on its low stability constants with sorption constants pH conditions, and high potential for toxicity for microbes as well as its high adsorption constants with activated carbon, and its use in industrial processes. Cadmium(II) ions sorb to many different types of activated carbon at pH values between 1 and 9. At higher pH values, the metal precipitates out of solution as $Cd(OH)_2$ salts. At lower pH, carbon surface sites can become increasingly protonated, so cadmium cation sorption decreases. Between pH 1 and pH 6, cadmium adsorption increases by a factor of 10. Cadmium toxicity to microbes commonly occurs through thiol binding, protein denaturation, and interference with zinc and calcium metabolism. Some acidophiles have been reported to develop resistance to high levels of cadmium, but given its obvious absence in concrete (wastewater) environments, genetic resistance cassettes are not present. Chromate ($CrO_4^-$) ions were selected for use in an alternate test formulation, because they in the toxic Cr(VI) state and are also commonly found in industrial waste streams. Chromate and other Group V and VI anions inhibit thiosulfate oxidation in *Halothiobacillus neapolitanus* strains.

Embodiments of the formulation of the present disclosure can be produced using powdered activated carbon, granular activated carbon, or other carbon-based sorbents as the sorptive material, including but not limited to fly ashes and biochars. In Applicants' empirical studies, small-grained granular activated carbon (GAC) was loaded with metal ions by being shaken in a reactor containing 5 mM solutions of cadmium sulfate ($CdSO_4$) or potassium chromate ($K_2CrO_4$). Batches were shaken for 2 days, and the loaded GAC was rinsed three times and dried at 60° C. Aliquots of the metal solution before and after shaking were collected to determine metal loading rates. Metal quantitation was performed by the Laboratory for Environmental and Geological Studies, Department of Geology, University of Colorado. Loading rates were on the order of 1 mg metal/g carbon or one part per thousand. Suitable loading rates can be in the range, for example, of 0.01-100 mg metal/g carbon. Metal loading can be considered in calculations conducted to determine the amount of formulation needed per area or per volume of concrete to be treated, with a target application rate of approximately 5-50 mg metal per square meter of treated surface or approximately 100-500 mg metal per cubic meter of concrete.

For purposes of Applicants' empirical testing, one inch cubic concrete samples were formulated using ASTM standard C192. Selected samples were surface-treated with one of three treatments—unloaded GAC (no metals), cadmium-loaded GAC, or chromate-loaded GAC—by coating with a thin layer of hydrated Portland cement paste (about 5 mm thick) and applying the appropriate GAC at a surficial loading rate of approximately 1 to 5 g GAC per square meter (with approximately 1-5 mg metal per g GAC) of surface. Treated and untreated concrete samples were exposed to corrosive environments in working sanitary manholes and sampled periodically over one year. FIG. 4 is a photograph illustrating four samples wherein each sample was exposed to the same corrosive environment for the same amount of time. The samples were exposed for ten months to an extraordinarily corrosive environment which was found in an otherwise ordinary sewer manhole. Sample 1 was untreated; Sample 2 was covered with an activated carbon containing surficial layer prior to exposure; Sample 3 was covered with a cadmium-loaded activated carbon containing surficial coating prior to exposure; and Sample 4 was covered with a chromium-loaded activated carbon containing surficial coating layer prior to exposure. Samples 3 and 4, treated with heavy metal containing coatings, clearly experienced remarkably less corrosion as judged by mass loss than did Samples 1 and 2. Loss of mass exhibited by untreated Sample 1 was severe, on the order of 40%.

Embodiments of the present application include addition to concrete mixtures for new structures including those cast in place or precast, incorporation into non-cementitious concrete coatings or treatments, such as epoxy or cured-in-place pipe lining, and addition to cementitious material, such as shotcrete or calcium aluminate cements, for surficial application.

Embodiments disclosed herein can be utilized for the purpose of preventing corrosion in any suitable environment such as, by way of non-limiting example, wastewater infrastructure, water treatment and distribution infrastructure, petroleum refining and transportation infrastructure, subsurface well casings and supports, hydraulic fracturing wells and natural gas storage and/or transportation infrastructure. In the context of wastewater collection and treatment infrastructure, protection can be applied to common appurtenances at least for manholes, wet wells, pump stations, pipes, clarifiers and channels. Embodiments of the present disclosure can be used in place of existing commercial concrete coatings such as, for example, those described above, which can be comparatively expensive and typically do not inhibit the corrosion process at its fundamental beginnings—the metabolism of acidogenic microbes.

In addition to the disclosed protected structures, also disclosed herein are methods of producing a protected structure. In one aspect, disclosed herein are methods for producing a protected structure in an environment that subjects the protected structure to microbially induced concrete corrosion, said method comprising adding a formulation of heavy metal-laden, carbon-based sorbent to a cementitious material to form the protected structure such that the formulation limits the microbially induced concrete corrosion during exposure of the protected structure to the environment.

Also disclosed are methods for producing a surficial coating for a concrete structure that is to be exposed to an environment that subjects the concrete structure to microbially induced concrete corrosion, said method comprising adding a formulation of heavy metal-laden, carbon-based sorbent to a base material (such as, for example a cementitious material as disclosed herein) to form the surficial coating.

It is understood and herein contemplated that the disclosed compositions can be used to produce a protective additive for use in existing concrete structures. Therefore, in one aspect, disclosed herein are methods for producing an additive for use in protecting a concrete structure from an environment that subjects the concrete structure to microbially induced concrete corrosion, said method comprising producing a formulation of heavy metal-laden, carbon-based sorbent; and mixing the formulation with a base material (such as, for example a cementitious material) to form the additive.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

B. EXAMPLES

Microbially induced corrosion of concrete wastewater infrastructure is associated with billions of dollars in rehabilitation costs each year. This phenomenon is caused by sulfur-oxidizing microbial communities that grow on hydrogen sulfide and reduced sulfur compounds in the headspace of wastewater conveyance and treatment structures. The occurrence of corrosion has increased markedly in the past 30 years as a result of industrial wastewater pre-treatment legislation, and will continue to increase due to ageing systems, climate change, and (sub)urbanization. Current prevention and treatment technologies are relatively expensive and do not target the causative microbiology.

In response to this widespread problem, the objectives of this disclosure are to characterize the spatial and temporal trends in corrosion-associated microbial communities and to develop cost-effective engineering controls to prevent corrosion by inhibiting acidogenic biofilms in situ. Corroded concrete was collected from ten utilities in the United States and from specimens exposed in a manhole for between one and twelve months. Corrosion was found to be most severe in sites with high levels of gaseous hydrogen sulfide and carbon dioxide. These sites were characterized by concrete binder degradation, pore water pH values below 1, and low microbial diversity (less than 10 taxa). Severely corroded concrete was colonized primarily by acidophilic sulfur-oxidizer *Acidithiobacillus* spp. Early-stage corrosion communities were associated with neutral pore water pH and higher microbial diversity, including neutrophilic sulfur-oxidizers and heterotrophs. Bacterial community succession on exposed concrete specimens was similar to that described by culture-based bacterial models. However, an acidophilic euryarchaeon, *Ferroplasma* spp., was observed in extreme corrosion communities.

A novel concrete formulation amended with activated carbon impregnated with heavy metals was designed to locally inhibit sulfur-oxidizing activity in response to local pH depression. Treated and untreated specimens were exposed in sanitary manholes for up to a year. Treated samples experienced significantly less corrosion than otherwise identical untreated samples, even though the bacterial community compositions of surface biofilms were similar. This formulation can be manufactured with reused metal from industrial wastes and is expected to be several orders of magnitude cheaper than competing products.

1. Example 1: Assessment of Remediation Strategies

Described herein are methods and compositions used to develop and test a novel cement admixture formulation designed to inhibit the activity of sulfur-oxidizing biofilms and subsequent corrosion through pH-dependent release of metal ions on the micro-scales relevant to in situ bacterial activity. This formulation is expected to be competitive both functionally and economically with commercially available concrete coating treatments. While current coating technology can often protect concrete surfaces from biogenic acids, they do not inhibit microbial activity or associated acid production in situ. In some cases, corrosion can continue under the coatings when hydrogen sulfide diffuses through them, or acid leaks through gaps or perforations. In addition, coating efficacy is highly dependent on the skills of the operators applying a coating. Several companies sell antimicrobial coatings or metal-based additives that can inhibit of corrosion-causing biofilms, but production remains relatively expensive in this market sector. The disclosure herein completes, develops and applies a low-cost, pH-responsive concrete formulation to inhibit corrosion-causing biofilms. This concept was then forwarded to field trials in the most corrosive locations identified in the regional survey. The use of carbon-based sorbent for pH-dependent release of metals to inhibit detrimental biofilms has not previously been applied.

In the context of treating waste streams with high metal loads, heavy metal sorption to activated carbon has been well studied and applied to practice. The formulation tested here intentionally reverses this removal process in a controlled and targeted manner for the express purpose of inhibiting microbially induced corrosion. It can be manufactured sustainably using waste materials and is expected to be several orders of magnitude less expensive than current rehabilitation products.

In this research, powdered activated carbon (PAC) loaded with cadmium ($Cd^{2+}$) or chromate ($CrO_4^{2-}$) ions was tested for its ability to impair the growth of sulfur-oxidizing cultures in the laboratory. Additionally, granular activated carbon (GAC) loaded with the same metals was surface-applied to concrete and tested for corrosion prevention efficacy in two working sanitary manholes on the front range of Colorado. Treated specimens were compared to untreated specimens on the basis of mass loss, pH depression, and bacterial community characteristics as measured by V1V2 16S rRNA amplicon sequencing.

a) Metal Desorption Characteristics

The metal leaching behavior of the GAC impregnated with $Cd^{2+}$ or $CrO_4^{2-}$ ions was determined using phosphate or citrate buffer solutions as described herein. Cadmium desorption showed a strong pH dependency, with increasing desorption at pH values below 6 (FIG. 5). This is consistent with studies that found cadmium and other metal cations sorbed to activated carbon most strongly at high pH. On the other hand, chromate anion appears to sorb strongly at pH above 7 and pH below 5. Also, chromate anions have increased sorption to activated carbon at low pH.

The window from pH 5 to pH 7 is the ideal range for metal ion desorption to inhibit corrosion biofilms for several reasons: a.) at these pH values, corrosion is initiated but does not progress at a rate which causes serious deterioration and b.) this is the range where diverse neutrophilic sulfur-oxidizing communities are replaced by low-diversity acidophilic communities. By delivering toxicity in the pH range where this transition between community types occurs, the metal-carbon formulations can prevent acidophile colonization. These results indicate that both cadmium cations and chromate anions desorb from pre-loaded granular activated carbon in a pH range that is germane to biofilm activity in corroding sewer infrastructure. Cadmium cation sorption is more ideal for this corrosion prevention application because metal remains in solution as corrosion progresses to pH values below 6. While chromate ions can resorb onto the carbon below pH 4 (FIG. 5), this does not dampen their effectiveness in the target pH range of pH 5 to pH 7.

b) Laboratory Testing of Growth Inhibition in Liquid Media

Both liquid and solid media inhibition experiments were attempted with the goal of testing inhibition of sulfur-oxidizing bacterial growth in the presence of the metal-carbon formulations through a range of pH values relevant to the corrosion process. Cultures used in liquid testing are ATCC pure cultures of *Acidithiobacillus thiooxidans* (ATCC #19377) and *Thiobacillus thioparus* (ATCC #23646) and an enrichment culture from severely corroded concrete comprised of over 99% *Acidithiobacillus* spp. as judged by Illumina MiSeq bacterial V1V2 16S amplicon sequencing. Both of these genera have been previously implicated in the corrosion process and were observed at multiple sites in the regional corrosion survey conducted as part of this disclosure.

Several methods for quantifying bacterial growth were tested. Optical density was not directly correlated to cell concentrations, because precipitates in the media were abundant and depended on pH. Redox-based growth indicators resazurin, CTC tetrazolium salt (5-cyano-2,3-ditolyl tetrazolium chloride), and INT tetrazolium salt (2-p-iodophenyl-3-p-nitrophenyl-5-phenyl tetrazolium chloride) were tested, but all these compounds were found to inappropriately reactive to acidic pH as well as redox conditions, so they could not be used throughout the experimental targeted pH range. The phospholipid biomass assay described herein was also tested for growth quantitation, but biomass differences in the range of growth examined could not be resolved. In addition, the phosphate concentration included in growth media for its buffering capacity caused interfering backgrounds in phospholipid assay blanks. Sulfur oxidizer growth was not directly related to optical density, so cell counting by epifluorescence microscopy was required to quantitate growth responses.

Water chemistry modeling with Visual MINTEQ indicated that salt concentrations in the sulfur-oxidizing ATCC 290 medium used complexed over 90% of cadmium and chromium. To address this issue, the amount of metal-carbon formulation added to treated wells was increased by a factor of 10 in order to ensure toxic concentrations of free metal ions could be liberated into test-solutions under acidic conditions. However, this increase in activated carbon increased the pH instability of the cultures.

TABLE 1

Expected cadmium and chromium speciation in liquid media at pH 3 and pH 5. Total metal concentrations based on leaching experiments in media, metal speciation modeled with Visual MINTEQ software.

|  | pH 3 | | pH 5 | |
|---|---|---|---|---|
| Cadmium Species | Concentration [mM] | Percent of Total Cd | Concentration [mM] | Percent of Total Cd |
| $Cd^{+2}$ | 9.27E−06 | 0.0% | 5.66E−06 | 0.0% |
| $Cd(NH_3)_2^{+2}$ | 8.20E−13 | 0.0% | 4.92E−09 | 0.0% |
| $Cd(NH_3)_3^{+2}$ | 2.84E−17 | 0.0% | 1.68E−11 | 0.0% |
| $Cd(NH_3)_4^{+2}$ | 2.89E−22 | 0.0% | 1.70E−14 | 0.0% |
| $Cd(OH)_{2\,(aq)}$ | 2.31E−19 | 0.0% | 1.41E−15 | 0.0% |
| $Cd(OH)_3^-$ | 3.05E−29 | 0.0% | 1.86E−23 | 0.0% |
| $Cd(OH)_4^{-2}$ | 4.78E−41 | 0.0% | 2.91E−33 | 0.0% |
| $Cd(S_2O_3)_2^{-2}$ | 8.11E−01 | 91.1% | 8.27E−01 | 93.0% |
| $Cd(S_2O_3)_3^{-4}$ | 1.15E−04 | 0.0% | 1.52E−04 | 0.0% |
| $Cd(SO_4)_2^{-2}$ | 2.76E−07 | 0.0% | 2.78E−07 | 0.0% |
| $Cd_2OH^{+3}$ | 1.84E−17 | 0.0% | 6.85E−16 | 0.0% |
| $CdCl^+$ | 1.29E−04 | 0.0% | 1.02E−04 | 0.0% |
| $CdCl_{2\,(aq)}$ | 8.84E−06 | 0.0% | 9.09E−06 | 0.0% |
| $CdHPO_{4\,(aq)}$ | 3.41E−06 | 0.0% | 8.62E−05 | 0.0% |
| $CdNH_3^{+2}$ | 5.19E−09 | 0.0% | 3.14E−07 | 0.0% |
| $CdOH^+$ | 4.87E−12 | 0.0% | 2.97E−10 | 0.0% |
| $CdS_2O_{3\,(aq)}$ | 7.90E−02 | 8.9% | 6.24E−02 | 7.0% |
| $CdSO_{4\,(aq)}$ | 3.26E−05 | 0.0% | 2.56E−05 | 0.0% |
| Total Cadmium | 8.90E−01 | | 8.90E−01 | |

|  | pH 3 | | pH 5 | |
|---|---|---|---|---|
| Chromium Species | Concentration [mM] | Percent of Total Cr | Concentration [mM] | Percent of Total Cr |
| $Cr_2O_7^{-2}$ | 4.56E−04 | 10.0% | 3.91E−04 | 47.6% |
| $CrO_4^{-2}$ | 3.20E−07 | 0.0% | 2.96E−05 | 3.6% |
| $CrO_3Cl^-$ | 9.72E−07 | 0.0% | 1.18E−08 | 0.0% |
| $CrO_3H_2PO_4^-$ | 3.12E−03 | 68.3% | 1.23E−05 | 1.5% |
| $CrO_3HPO_4^{-2}$ | 9.85E−04 | 21.6% | 3.89E−04 | 47.3% |

TABLE 1-continued

Expected cadmium and chromium speciation in liquid media at pH 3 and pH 5. Total metal concentrations based on leaching experiments in media, metal speciation modeled with Visual MINTEQ software.

| $CrO_3SO_4^{-2}$ | 9.96E−07 | 0.0% | 1.19E−08 | 0.0% |
|---|---|---|---|---|
| Total Chromium | 4.56E−03 | | 8.22E−04 | |

Controlling the pH of experimental cultures in the presence of metal-laden PAC was important to maintain a relatively stable environment for bacterial growth and to assess the potential effect of the toxicity of these formulations at different pH values. The powdered activated carbon used for this proof-of-concept study had a high buffering capacity, neutralizing up to 3 moles of acid per kilogram carbon over the course of two weeks. While this characteristic is advantageous for treating corroding concrete, it impedes rigorous laboratory testing. As a result, culture solutions in wells treated with carbon experienced significant increases in pH that were rapidly initiated. To address this issue and help stabilize pH, acid was added every day during the course of 12-day enrichment experiments to maintain pH in targeted ranges and in a series of parallel experiments, the carbon's expected acid adsorption capacity (3 moles acid/kg carbon) was added to un-innoculated wells and allowed to equilibrate for two weeks before starting the growth assay.

c) Laboratory Testing of Growth Inhibition in Solid Media

Growth inhibition testing on solid culture media was also executed with an experimental design analogous to classical antibiotic resistance screening. These experiments were complicated by the difficulty of growing autotrophs on solid media and by the high sorption capacity of the carbon. Only one sulfur oxidizing culture (the Acidithiobacilius enrichment) was successfully grown on solid media. Solid agar media is a relatively dry and oxidizing environment, and is less amenable to hosting these types of microbes than liquid media. Once this culture was successfully grown on solid agar media, experiments were further complicated by the propensity for activated carbon to sorb nutrients from the media. Inhibition zones were observed around both unloaded and metal-loaded carbon, indicating that the carbon sorption was inhibiting cell growth. Crystalline structures about 100 μm in length were observed on and around the activated carbon grains, and originated from salts removed from the growth medium. Further testing was subsequently abandoned.

TABLE 2

Installation and sampling schedule for three field tests using treated and untreated samples (I indicates sample installation, X indicates specimen removal)

|  |  | 2011 | | | 2012 | | | | | | | | | | |
|---|---|---|---|---|---|---|---|---|---|---|---|---|---|---|---|
| Experiment | Manhole | O | N | D | J | F | M | A | M | J | J | A | S | O | N | D |
| A | MH2 (Moderate) | | | I | X | | X | | X | | X | | X | | X | | X |
| B | MH1 (Severe) | | | | | | | | | | I | X | X | X | X |
|  |  | | | | | | | | | | | | X | | X | |
| C | MH1 (Severe) | I | | X | X | | X | | X | | X | | X | | X | |

Under the most corrosive field conditions used in this study (MH1) (Experiments B and C), specimens treated with a surficial cement coating containing cadmium- or chromate-loaded granular activated carbon experienced significantly less corrosion as judged by surface area corrosion and dry mass loss when compared to untreated samples (ANCOVA $p<0.005$) (FIG. 6 and FIG. 7). In MH2 (Experiment A), corrosion was less severe (<10% mass lost and <20% surface corrosion). When considering all data points, no significant differences in surface area corrosion or mass loss were observed between treated and untreated specimens in either manhole. However, treated specimens exposed for eight to twelve months in MI-11 experienced less mass loss and surface corrosion than otherwise identical control specimens (FIG. 6). After four months, treated specimens were characterized by red and black surface coloring (FIG. 7). Some treated specimens experienced corrosion only where they touched the plastic sample holder casing (as in FIG. 7, top right corner), which introduced and unfortunate experimental artifact. This corrosion was caused by sulfuric acid produced by bacteria growing on the casing surface that inadvertently dripped onto the specimen (FIG. 8). For this reason, it is expected that the corrosion prevention capacity of the treatment is underestimated by these results.

Some mildly-corroded specimens gained dry mass over the experiment. This is a result of biologically-produced sulfate being incorporated into minerals such as gypsum. The source of the sulfate is gaseous hydrogen sulfide and oxygen, which is not part of the original specimen mass.

e) Field Testing: Cadmium and Chromium in Treated Samples

Cadmium and chromium were measured in dry sieved corrosion products for the treated samples in Experiment B, and are presented both as ng/g dry sieved fines as well as μM in pore water (FIG. 9). These metals are typically present in Portland Cement at average concentrations of 0.34 ng/g Cd and 76 ng/g Cr. Generally, metals concentration observed in treated corroded concrete in this study were significantly higher than expected background concentrations, indicating that the metal-carbon formulation successfully released metal ions at the corrosion front. Aside from one chromium outlier at 71 days, metal concentrations in the dry fine material after 50 days stayed relatively constant between 400 and 800 ng/g. This timing of metals release corresponds to a concomitant decrease in pore water pH for both cadmium- and chromate-treated specimens from pH 12 to pH 2 occurring between 49 and 71 days of field exposure.

Metal concentrations—micromolar levels of both cadmium and chomium—in pore water are also shown; these levels represent the concentrations which drive metal diffusion into bacterial cells on the corrosion front. Pore water concentrations increased to several μM after 70 days, and subsequently receded to less than 0.2 μM by the end of the experiment at 126 days (FIG. 9). This decrease is in pore water concentrations is due to a marked increase in surface moisture as the experiment progressed (up to 23% moisture), which diluted the released metal ions. Cadmium and chromium at μM concentrations have been shown to inhibit bacteria involved in wastewater treatment under certain conditions and are about an order of magnitude higher than typical concentrations observed in municipal wastewater. While many studies have shown acidophilic sulfur oxidizing bacteria can be resistant to mM concentrations of metals in mining environments, the lack of selection pressure in wastewater systems and the location of corrosion on the sewer crown (away from wastewater flow) suggests that corrosion biofilms are unlikely to harbor or acquire metal resistance genes.

f) Field Testing: Microbial Community Composition

In all carbon treatments (Blank GAC, Cadmium GAC, and Chromate GAC) in the three respective longitudinal experiments, biofilm communities followed a trend of neutrophiles to acidophiles and high α-diversity to low α-diversity (often less than 50 taxa) (FIG. 10). This trend matches community shifts observed on untreated concrete specimens in the longitudinal survey portion of this research.

This community succession appears to occur more rapidly on chromate-treated samples than on untreated or cadmium-treated samples. The activated carbon used here presented a relatively high acid neutralization capacity as tested in the lab, so the blank carbon treatment had a buffering effect that slowed surface acidification. This explains why the untreated carbon harbored neutrophiles longer than the chromate-treated carbon, as the chromate may be loaded onto surface sites that would otherwise be used sorb $H^+$ ions and slow the pH drop.

The communities observed on all three types of GAC treatments were initially dominated by the bacterial family Halothiobacillaceae, a neutrophilic sulfur-oxidizing group that has been observed in early-stage communities (FIG. 10). On the blank and cadmium GAC treated specimens. *Brevundimonas* spp. sequences were detected during the intermediate corrosion stage in MH2. This genus is involved in a neutrophilic, heterotrophic lifestyle using microbial by-products of sulfur-oxidizers as substrates.

After four months of exposure in MH1 or ten months of exposure in MH2, bacterial communities on both treated and untreated specimens contained over 80% *Acidithiobacillus* spp. sequences, as judged by V1V2 region Illumina sequencing. This taxa is also the dominant community member observed in late-stage corrosion and in severely corroded biofilms in the literature. These microbes have been observed to thrive in metal-rich acid mine drainage environments, but cells present in the wastewater environment are expected to uptake or maintain heavy metals resistance genes, because municipal wastewater is regulated to very low levels of metals (parts per billion).

g) Field Testing: Phospholipid Biomass Estimates

Sample biomass was estimated by measuring lipid-associated phosphate as described herein. As judged by phospholipids, the untreated samples and blank carbon-treated samples experienced similar trends of accumulating biomass (FIG. 11). In the more severe MH1 (Experiments B and C), biomass increased on the untreated specimens more rapidly than on otherwise identical specimens with entrained metal-GAC formulation. Under more moderately corroding conditions (Experiment A in MH2), biomass appeared to decrease slightly between two months and eight months, and then increased at ten months. This is due to a microbial selection response to pH as populations transition between neutrophilic and acidophilic regimes.

For the cadmium-treated carbon and chromate-treated carbon treated samples in MH1, biomass notably increased during the initial two months and stayed relatively for the duration of a year. Under highly corrosive conditions in MH1 ($H_2S>300$ ppm), estimates of biomass accumulating on specimens which incorporated metal-GAC formulations were significantly lower than untreated concrete specimens (ANCOVA p<0.01), indicating that the treatment inhibited biofilm production. Under moderately corrosive conditions in MH2, metal-GAC treated specimens did not follow the same biomass accumulation trends. This is because corrosion in this manhole did not progress to a phase where significant acidophilic populations developed in the observation period of one year.

h) Field Testing: Electron Microscope Images of Corroding Concrete

Environmental scanning electron microscopy (ESEM) was used to characterize surface morphology of raw concrete that had not been exposed to a corrosive environment and the surfaces of untreated and metal-GAC treated samples that had been exposed to a high $H_2S$ environment in MH1 for 110 days.

The raw (unexposed) concrete surface that was imaged was a cut face of the same type of concrete specimens that were exposed to corrosive environments in manholes. At a macro scale, about 70% is cement binder and small aggregate, and about 30% is the cut face of large aggregate. On a small scale, the binder and small aggregate surface was characterized by smooth faces of aggregate and small cement binder crystals on the order of 1-5 μm in size. This is smaller than the 5-40 μm calcium oxides crystals in Portland cement. The micrometer scale view of the cut aggregate surface showed smooth flat surfaces with angular breaks between them. Elemental electron diffraction data indicates that this portion of the surface is composed of >90% silicon oxides. The surfaces with cement binder crystals are primarily composed of carbonates along with calcium, silicon, potassium, and aluminum, which is consistent with the composition of Portland cement.

The surface of exposed untreated concrete was typified by sharp blocky crystalline structures. About 40% of the surface had large crystals with greater than 10 μm long, and the remaining surface had smaller crystals about 1-10 μm long. The large crystals were comprised of only sulfur, while the smaller crystals also contained calcium and oxygen, indicating the possible presence of gypsum. This morphology is markedly different than that of unexposed concrete, and reflects the chemical changes associated with microbially induced corrosion and its byproducts.

The surface of exposed cadmium-treated concrete also had crystalline shapes, but the crystals were generally more rounded. The crystals were very tightly packed over about 30% of the surface. About 40% of the surface was characterized by a loosely-packed layer of these same crystals underlain by long, vertically-oriented crystals. Another 20% of the surface had rounded, pocked crystals 10-30 μm in diameter, and 10% of the surface had round non-crystalline shapes 1-10 μm in diameter. The surface morphology of the treated cube exposed to the high $H_2S$ atmosphere is markedly different than that of the untreated, exposed sample. When considered in conjunction with the lower mass loss and surface area corrosion observed on treated specimens, this analysis indicate that the corrosion inhibition mechanism associated with the metal-carbon formulation affects the microscale crystal structure of the concrete surface.

2. Example 2: Feasibility of Using Metal-Carbon Cement Formulation to Inhibit Corrosion Potential technical impediments to practical application of the formulation include the potential for biofilms to develop metals resistance and concern about the ultimate fate of released metals. The uptake of a "resistance gene" cassette has been observed to confer protection to relatively high (mM) concentrations of heavy metals under various environmental conditions. However, cells have energetic motivation to excise DNA that is not being used, so significant amounts of metal resistance genes are only expected in environments where (the targeted) metals exist under sustained conditions or have recently existed. While the use of surface-applied metal-carbon formulation contributes to heavy metal selection pressure, the pH-dependent release of metal ions is intermittent in response to pH depression, and released metals are ultimately removed from pore water to form precipitates with reduced sulfur species. As a result, the heavy metal selection pressure needed to acquire and maintain heavy metal resistance genes is absent or inconsistent at the pipe crown. In addition, the release of heavy metal from the activated carbon sorbent is expected to be localized on micrometer scales.

The only significant potential source of metals or metal resistance genes to the corroding concrete on unwetted sections of wastewater collection and treatment structures is the wastewater flow itself, which could reach the corrosion through splashing or aerosolization of bacterial cells. Because heavy metals are not able to enter a gaseous phase in sewers, they can only reach the corroding sections by aqueous transport. This is a significant transport mechanism in wastewater collection systems with combined sewer overflows, as rain events can cause pipes to flow full. However, in segregated wastewater collection systems, a full pipe is a poorly designed pipe, and the incidence of wastewater reaching the pipe crown is low. Based on average per capita residential discharge of cadmium and chromium to municipal wastewaters from a 1994 review, and using Boulder, Colo.'s 20 MGD wastewater treatment facility serving 90,000 persons as an example, expected concentrations in municipal wastewater are on the order of 2 μg Cd/L (20 nM) and 9 μg Cr/L (180 nM). Another study in France found concentration to be less than 1 μg Cd/L and 5 μg Cr/L. These levels of cadmium and chromium in wastewater collection systems suggest that resistance to these metals are not abundant. Further, the pH, alkalinity, and particle loads typical of raw sewage suggest that metals in these concentrations are complexed, sorbed, or otherwise removed from the aqueous phase. In collection systems receiving large amounts of wastewater from metal-processing industries, these effluents exert a selection pressure that favors resistance and can contain transferrable heavy metals resistance genes. However, the atmospheric barrier between the wastewater flow and the corroding pipe crown limits heavy metal selection pressure in corroding concrete, so resistance genes do not persist.

Another aspect of the tested metal-carbon formulation that concerns potential users is the ultimate fate of the heavy metals introduced to the wastewater collection system. However, the amounts of metal released by these metal-carbon formulations are relatively small and localized. For the treatment of one manhole, approximately 1 g of metal can be applied and released intermittently over a term of years in response to pH depression. Even if all of this metal is desorbed from the GAC and entered the wastewater flow in one day, a 20 MGD plant would see an increase of 50 ng/L metal in plant influent from a single manhole. Since typical levels of metal in wastewater influents are 1-100 μg/L, the metal released from the carbon would not significantly affect the plant's influent concentration. Also, the metal ions are strongly bound to the activated carbon and are only release in a localized corrosion front associated with low surface pH conditions in high $H_2S$ headspaces. Any metal liberated, rapidly precipitates as a sulfide. These environments exist as a result of high sulfide concentrations in wastewater, so any metal entering the wastewater flow in these environments forms insoluble metal sulfides and be removed from the aqueous phase. Regardless, aqueous exchange between the corroding pipe crown and the wastewater flow is expected to be minimal, so the released metal ions are expected to ultimately precipitate as insoluble metal sulfides in the corrosion matrix.

The metal-carbon formulations developed here can be manufactured at a low cost, because all of the required materials can obtained or produced from industrial or agricultural waste streams. Electroplating industries produce highly acidic wastewaters containing heavy metals of interest that is treated at high cost before being discharged to municipal sewers or waterways. Metals from industrial plating waste streams contain large concentrations of metals, including cadmium, chromium, nickel and zinc. These waste streams are low pH and must be treated to stringent industrial waste standards before their disposal. These companies can redirect a portion of those wastes to activated carbon impregnation, creating a symbiotic relationship where they can spend less to manage metal wastes and the commercial sector can acquire metals for very low cost. Likewise, activated carbon for this application can be purchased at low cost from operations that produce it from agricultural by-products. This makes the treatment both low-cost and sustainable. Preliminary cost estimates indicate that this formulation can be manufactured and sold at $25 per kilogram or per 10 cubic yards shotcrete, which is an order of magnitude less than the price of CONMICSHIELD®, a competing corrosion inhibition product.

The present application demonstrates the effectiveness and feasibility of a corrosion-inhibiting, metal-carbon formulation that can be cost-effectively manufactured using recycled materials. Treated specimens in a severely corrosive environment experienced significantly less corrosion and presented different microscale surface morphology despite harboring similar microbial communities. Based on results from the survey, which indicate that microbial communities associated with corrosion are similar on regional scales, similar corrosion-inhibition responses are expected regardless of locale. Additional results from both the regional survey and the longitudinal study indicate that late-stage corrosion communities have very low α-diversity, which indicates that they are relatively susceptible to engineering controls, having the potential for less biological resilience than more diverse communities.

The potential for biofilms to develop heavy metal resistance and for these formulations to release metals to the wastewater flow are two potential flaws of this approach. However, the low concentrations of metals in municipal wastewater and the physical distance between the flow and the corrosion mean that heavy metals resistance genes are not abundant or available to microbes in corroding concrete on sewer pipe crowns. In addition, the high solubility constants of metal sulfides mean that what when metal is released, it is not bioavailable for activated sludge biofilms, and released metals end up in wastewater biosolids at extremely low concentrations. Any metals liberated in response to depressing pH in a corrosion front are retained in the gypsum/ettringite corrosion matrix as insoluble metal sulfides.

Potential applications of the formulation include addition to concrete formulations, incorporation into non-cementitious concrete treatments, and addition to cementitious surficial treatments for the purpose of preventing corrosion in wastewater infrastructure, water infrastructure, petroleum infrastructure, hydraulic fracturing wells, and natural gas infrastructure—any environment there sulfur drives detrimental biofilm activity. In contrast to many widely used corrosion prevention strategies, this formulation directly targets the source of the problem—sulfur-oxidizing microbial metabolism. Whether applied proactively or retroactively to concrete in highly corrosive environments, this novel formulation has significant potential for enabling corrosion prevention around the world in a cost-effective manner.

3. Example 3: Geographic Survey of Concrete Corrosion Characteristics

Two distinct community types observed coincided with moderate and severe corrosion, respectively. Highly corroded sites have very low α-diversity, typically less than five observed taxa, and are dominated by *Acidithiobacillus* spp., sometimes in conjunction with *Acidiphilium* spp. and *Mycobacterium* spp. These sites were characterized by high concentrations of both H2S (>10 ppm) and CO2 (>10,000 ppm), low pore water pH (<2), and high moisture content of corrosion products. In contrast, mild corrosion typically occurred in sites with lower levels of H2S and CO2 gas and supported a more diverse community that included heterotrophic and nitrogen-fixing genera. Methane concentrations were not observed to have an effect on either corrosion severity or microbial community composition. Based on Sanger sequencing using universal primers, the community observed on an untreated specimen was markedly different than communities observed on specimens treated with commercial corrosion-prevention treatments. The untreated concrete hosted a community dominated by the archaeal genus *Ferroplasma*.

4. Example 4: Microbial Community Succession pH is the master environmental variable related to corrosion severity. Depressed pH occurs in response to biogenic sulfuric acid production associated with the metabolism of sulfur-oxidizing microbial communities. As corrosion progresses, the microbial community associated with a concrete surface changes from relatively diverse communities (α-diversity>25 taxa) dominated by neutrophilic sulfur-oxidizing bacteria (primarily *Halothiobacillus* spp.) to low diversity communities (α-diversity<5 taxa) dominated by acidophilic sulfur-oxidizing genus *Acidithiobacillus* spp. This trend was observed in two adjacent manhole environments with markedly different corrosion rates. In the first reported instance of archaea in a significant role in a corrosion environment, the iron-oxidizing archaea *Ferroplasma* spp. appear to dominate in some late-stage communities. In short, corrosion associated communities follow a distinct succession of neutrophiles to acidophiles and decreasing α-diversity in response to decreasing pore water pH.

5. Example 5: Remediation Strategy Design and Testing

When alone is solution or entrained in cement, the metal-carbon formulation tested in this research releases metal ions in aqueous solutions when pH values drop below 5. These formulations are stable at neutral pH, where metals are strongly sorbed to carbon surfaces. When compared to otherwise identical untreated samples, concrete specimens treated with a surface application of metal-carbon modified cement experienced lower rates of surface corrosion and mass loss when exposed to corrosive field environments for up to a year. However, while treated concrete surfaces had lower estimated biomass than untreated surfaces, microbial community composition was similar between treated and untreated specimens. Preliminary laboratory culture work indicates that sulfur-oxidizing bacterial growth is inhibited by metal-carbon formulation, but extensive culture testing was unsuccessful.

6. Example 6: Synthesis

The overarching purpose of this work was to contribute to knowledge regarding spatial and temporal variations in microbial communities responsible for concrete corrosion in wastewater collection and treatment systems. A significant contribution of this research is an improved model connecting the various environmental factors that are correlated to severe concrete corrosion. This includes, but is not limited to, the enrichment of $H_2S$ and $CO_2$ in the headspaces of wastewater collection and treatment systems. Previous models generally do not consider $CO_2$ to be an accelerating factor. This environmental variable is a key consideration, since biogenic aced production in these environments is governed by autotrophic activity, which requires $CO_2$ as a carbon source.

The chemical, physical, and microbial properties of corroding concrete also change in response to environmental factors. Severe corrosion was found to result from a combination of several environmental factors, including $H_2S$ and $CO_2$ concentrations and exposure time (i.e. age of the concrete pipe or manhole). These corrosion-inducing factors were correlated to severe corrosion, as defined by pH, cement loss, moisture, and microbial community composition. Concrete dissolution presents failure risk, as the corrosion byproducts that replace cement binder are structurally unsupportive and can easily be removed concrete surfaces through sloughing and erosion. "Exposure," as a conglomerate of time and gas concentrations, appeared to dictate corrosion rate and extent. Using this conglomerate exposure as the primary composite variable, FIG. 12 summarizes the factors that promote corrosion juxtaposed with associated chemical, physical, and microbial parameters that drive the corrosion processes.

7. Example 7: Applications to Engineering Practice

Culture-based models of the corrosion process have been generally accepted in the wastewater arena, but many inspectors and engineers remain unfamiliar with the role of microbes in exacerbating corrosion. This research outlines an improved model of corrosion processes through a better understanding of microbial communities driving them. The improved model serves as a guide to corrosion processes to wastewater professionals.

The underlying corrosion mechanism indicated by these results is biogenic acid production by sulfur-oxidizing microbes. This acid then causes a series of chemical and physical changes that result in concrete deterioration. Treating massive amounts of wastewater to inhibit sulfide liberation in sewers is impractical and expensive, and surface treatments that do not inhibit acid generation are frequently ineffective. Design of corrosion prevention products can utilize the results of the present disclosure to focus on formulations that directly target the acidogenic microbial community. These low-diversity communities are expected to be especially susceptible to disruption by toxicity or environmental change.

The metal-carbon formulation tested here presents a low-cost corrosion inhibition approach with demonstrated success in corrosive field conditions. Similar formulations can be used in extremely corrosive environments in conjunction with an array of different concrete coatings to extend the life of pipe and other structures. Alternately, it can be applied on its own in mildly corrosive environments or on newly cured concrete pipe to provide low-cost corrosion prevention. Patent application for a provisional United States patent that includes these innovations has been filed.

C. REFERENCES

Bowker, R. P. G.; Smith, J. M.; Webster, N. A., *Odor and Corrosion Control in Sanitary Sewerage Systems and Treatment Plants*. Hemisphere Publishing: Washington, 1989.

Choubert, J. M., Pomies, M., Ruel, S. M., & Coquery, M. (2011). Influent concentrations and removal performances of metals through municipal wastewater treatment processes. *Water Science and Technology*, 63(9), 1967-1973.

ConMicShield, Anti-microbial additive provides corrosion protection for concrete in Canadian wastewater systems. *Concrete Plant International* 2011.

De Munyck, W.; De Belie, N.; Verstraete, W., Antimicrobial mortar surfaces for the improvement of hygiene conditions. *Journal of Applied Microbiology* 2010, 108, (1), 62-72.

De Muynck, W.; De Belie, N.; Verstraete, W., Effectiveness of admixtures, surface treatments and antimicrobial compounds against biogenic sulfuric acid corrosion of concrete. *Cement and Concrete Composites* 2009, 31, (3), 163-170.

Demiral, H., Demiral I, Tümsek, F., & Karabacakoğlu, B. (2008). Adsorption of chromium(VI) from aqueous solution by activated carbon derived from olive bagasse and applicability of different adsorption models. *Chemical Engineering Journal*, 144(2), 188-196.

Dopson, M.; Baker-Austin, C.; Koppineedi, P.; Bond, P., Growth in sulfidic mineral environments: metal resistance mechanisms in acidophilic micro-organisms. *Microbiology* 2003, 149, 1959-1970.

Haile, T.; Nakhla, G., A novel zeolite coating for protection of concrete sewers from biological sulfuric acid attack. *Geomicrobiology Journal* 2008, 25, (6), 322-331.

Hewayde, E. H.; Nakhla, G. F.; Allouche, E. N.; Mohan, P. K., Beneficial impact of coatings on biological generation of sulfide in concrete sewer pipes. *Structure and Infrastructure Engineering* 2007, 3, (3), 267-277.

Holt, S., *Thiobacillus* and microbial induced corrosion. *Coatings Pro Magazine* 2008.

Jenkins, D., & Russell, L. L. (1994). Heavy metals contribution of household washing products to municipal wastewater. *Water Environment Research*, 66(6), 805-813.

Kelly, D.; Shergill, J.; Lu, W.-P.; Wood, A., Oxidative metabolism of inorganic sulfur compounds by bacteria. *Antonie van Leeuwenhoek* 1997, 71, (1-2), 95-107.

Kelly, R.; Smolik, J., Restoring a corroded sewer. *Pipe Rehabilitation* 2011.

Kobya, M., Demirbas, E., Senturk, E., & Ince, M. (2005). Adsorption of heavy metal ions from aqueous solution by activated carbon prepared from apricot stone. *Bioresource Technology*, 96, 1518-1521.

Lawrence, C. D. (1998). The constitution and specification of portland cements. In P. C. Hewlett (Ed.), *Lea's Chemistry of Cement and Concrete*. New York, N.Y.: Wiley and Sons.

Leyva-Ramos, R.; Rangel-Mendez, J. R.; Mendoza-Barron, J.; Fuentes-Rubio, L.; Guerrero-Coronado, R. M., Adsorption of cadmium(II) from aqueous solution onto activated carbon. Water *Science and Technology* 1997, 35, (7), 205-211.

Sakamoto, K., Yagasaki, M., Kirimura, K., & Usami, S. (1989). Resistance acquisition of *Thiobacillus* thiooxidans upon cadmium and zinc ion addition and formation of cadmium ion-binding and zinc ion-binding proteins exhibiting metallothionein-like properties. *Journal of Fermentation and Bioengineering*, 67(4), 266-273.

Selvi, K., Pattabhi, S., & Kadirvelu, K. (2001). Removal of Cr(VI) from aqueous solution by adsorption onto activated carbon. *Bioresource Technology*, 80, 87-89.

Selvi, K.; Pattabhi, S.; Kadirvelu, K., Removal of Cr(VI) from aqueous solution by adsorption onto activated carbon. *Bioresource Technology* 2001, 80, 87-89.

Tsai, Y.-P., You, S.-J., Pai, T.-Y., & Chen, K.-W. (2005). Effect of cadmium on composition and diversity of bacterial communities in activated sludges. International Biodeterioration & *Biodegradation*, 55(4), 285-291.

Tyson, G., Chapman, J., Hugenholtz, P., Allen, E., Ram, R., Richardson, P., Solovyev, V., Rubin, E., Rokhsar, D., & Banfield, J. (2004). Community structure and metabolism through reconstruction of microbial genomes from the environment. *Nature*, 428, 37-43.

USEPA, Hydrogen Sulfide Corrosion in Wastewater Collection and Treatment Systems. Technical Report to Congress In EPA 430/09-91-010, 1991.

USEPA, Profile of the Fabricated Metal Products Industry. In EPA 310-R-95-007, 1995.

USEPA, Rehabilitation of Wastewater Collection and Water Distribution Systems. In EPA 600/R-09/048, 2009.

USEPA, Report to Congress on metal recovery, environmental regulation and hazardous waste. In EPA 530-R-93-018, 1994.

Valix, M., & Bustamante, H. (2010). *Sulfuric acid permeation in epoxy mortar coatings*. Paper presented at the 6th International Conference on Sewer Processes and Networks, Surfers Paradise, Australia.

Watkin, E. L. J., Keeling, S. E., Perrot, F. A., Shiers, D. W., Palmer, M. L., & Waiting, H. R. (2009). Metals tolerance in moderately thermophilic isolates from a spent copper sulfide heap, closely related to *Acidithiobacillus caldus, Acidimicrobium ferrooxidans* and *Sulfobacillus thermosulfidooxidans. Journal of Industrial Microbiology and Biotechnology*, 36(3), 461-465.

What is claimed is:

1. A composition comprising a cementitious substrate and heavy metal-associated granular activated carbon (GAC),
   wherein the GAC is present throughout the composition, and
   wherein, if the pH is about 5-7 at a given position of the composition, the GAC releases at least a portion of the heavy metal at the given position of the composition.

2. The composition of claim 1, wherein the composition is part of a cementitious or concrete structure substrate.

3. The composition of claim 1, wherein the composition is a surficial coating applied to a cementitious or concrete structure.

4. The composition of claim 1, wherein the composition is admixed with at least one other cementitious substrate.

5. The composition of claim 1, wherein the cementitious substrate comprises a non-hydraulic cement or hydraulic cement.

6. The composition of claim 1, wherein the heavy metal comprises at least one selected from the group consisting of cadmium, chromium, zinc, copper, silver, nickel, cobalt, lead, molybdenum, and tungsten.

7. The composition of claim 1, wherein the GAC has a surface area greater than about 500 $m^2/g$.

8. The composition of claim 1, wherein, if the pH is equal to or higher than about 7 at a given position of the composition, the GAC does not significantly release the heavy metal at the given position of the composition.

9. The composition of claim 1, wherein the heavy metal-associated GAC is prepared by contacting the GAC with a heavy metal solution with pH of about 7-9.

10. A method of preparing a concrete-containing structure that is resistant to microbially induced concrete corrosion, the method comprising preparing at least a portion of the concrete-containing structure using a composition comprising heavy metal-associated GAC and a cementitious material,
    wherein the GAC is present throughout the composition, and
    wherein, if the pH is about 5-7 at a given position of the composition, the GAC releases at least a portion of the heavy metal at the given position of the structure,
    whereby the concrete-containing structure is resistant to microbially induced concrete corrosion.

11. The method of claim 10, wherein the heavy metal comprises at least one selected from the group consisting of cadmium, chromium, zinc, copper, silver, nickel, cobalt, lead, molybdenum, and tungsten.

12. The method of claim 10, wherein, if the pH is equal to or higher than about 7 at a given position of the structure, the GAC does not significantly release the heavy metal at the given position of the structure.

13. A method of protecting a concrete-containing structure from microbially induced concrete corrosion, the method comprising coating at least a portion of the surface of the concrete-containing structure with a composition comprising a cementitious material and heavy metal-associated GAC,
    wherein the GAC is present throughout the composition, and
    wherein, if the pH is about 5-7 at a given position of the composition, the GAC releases at least a portion of the heavy metal at the given position of the coating composition.

14. The method of claim 13, wherein the concrete-containing structure comprises a non-hydraulic cement or hydraulic cement.

15. The method of claim 13, wherein the heavy metal comprises at least one selected from the group consisting of cadmium, chromium, zinc, copper, silver, nickel, cobalt, lead, molybdenum, and tungsten.

16. The method of claim 13, wherein, if the pH is equal to or higher than about 7 at a given position of the composition, the GAC does not significantly release the heavy metal at the given position of the composition.

17. A method of preparing a cement-based or concrete-based composition that is resistant to microbially induced corrosion, the method comprising mixing heavy metal-associated GAC with a cementitious substrate to form the composition,
    wherein the GAC is present throughout the composition, and wherein, if the pH is about 5-7 at a given position of the composition, the GAC releases at least a portion of the heavy metal at the given location of the composition.

18. The method of claim 17, wherein the cementitious substrate comprises non-hydraulic cement or hydraulic cement.

19. The method of claim 17, wherein the heavy metal comprises at least one selected from the group consisting of cadmium, chromium, zinc, copper, silver, nickel, cobalt, lead, molybdenum, and tungsten.

20. The method of claim 17, wherein, if the pH is equal to or higher than about 7 at a given position of the composition, the GAC does not significantly release the heavy metal at the given position of the composition.

* * * * *